US012593849B2

(12) United States Patent
Cuevas et al.

(10) Patent No.: US 12,593,849 B2
(45) Date of Patent: Apr. 7, 2026

(54) TEMPERATURE-OPTIMIZED BACILLI

(71) Applicant: Chr. Hansen A/S, Hoersholm (DK)

(72) Inventors: Patricia Dominguez Cuevas, Hoersholm (DK); Raquel Azevedo, Hoersholm (DK); Karin Bjerre, Hoersholm (DK); Iuliana Nita, Hoersholm (DK); Rute Neves, Hoersholm (DK); Lars Moelbak, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 880 days.

(21) Appl. No.: 17/638,152

(22) PCT Filed: Aug. 28, 2020

(86) PCT No.: PCT/EP2020/074126
§ 371 (c)(1),
(2) Date: Feb. 24, 2022

(87) PCT Pub. No.: WO2021/038072
PCT Pub. Date: Mar. 4, 2021

(65) Prior Publication Data
US 2022/0346384 A1      Nov. 3, 2022

(30) Foreign Application Priority Data

Aug. 29, 2019    (EP) ..................................... 19194343

(51) Int. Cl.
*A01N 63/22* (2020.01)
*C07K 14/32* (2006.01)
(52) U.S. Cl.
CPC .............. *A01N 63/22* (2020.01); *C07K 14/32* (2013.01)
(58) Field of Classification Search
CPC ................................ A01N 63/22; C07K 14/32

USPC ....................................................... 435/252.5
See application file for complete search history.

(56) References Cited

U.S. PATENT DOCUMENTS

2016/0183537 A1      6/2016   Taghavi et al.
2016/0183538 A1      6/2016   Taghavi et al.
2019/0191707 A1*     6/2019   Taghavi ................. A01N 25/10

FOREIGN PATENT DOCUMENTS

CN          110117560       *   8/2019
EP          2 287 179 A2       2/2011
WO          WO-02/29113 A2     4/2002
WO          WO-2008/066931 A2  6/2008

OTHER PUBLICATIONS

Du et al., Comparative genomic analysis of Bacillus paralicheniformis MDJK30 with its closely related species reveals an evolutionary relationship between B. paralicheniformis and B. licheniformis, BMC Genomics, vol. 20, No. 283, (2019), pp. 1-16.*
Albdaiwi et al., Draft Genome Sequence of Bacillus paralicheniformis Strain GSFE7, a Halotolerant Plant Growth-Promoting Bacterial Endophyte Isolated from Cultivated Saline Areas of the Dead Sea Region, American Society for Microbiology, Microbiology Resource Announcements, vol. 11, Iss. 9, (Sep. 2022), pp. 1-2.*
Mahapatra et al., Bacillus subtilis impact on plant growth, soil health and environment: Dr. Jekyll and Mr. Hyde, Journal of Applied Microbiology, vol. 132, (2022), pp. 3543-3562.*

* cited by examiner

*Primary Examiner* — Jennifer M.H. Tichy
(74) *Attorney, Agent, or Firm* — Adam Rucker

(57) ABSTRACT

The present invention relates to new strains of *Bacillus paralicheniformis* with improved growth rates and plant growth promoting properties and new strains of *Bacillus paralicheniformis* with improved growth rates when compared to their parental strains from where they are derived.

21 Claims, 8 Drawing Sheets

Specification includes a Sequence Listing.

Figure 7

TEMPERATURE-OPTIMIZED BACILLI

The present application is the U.S. National Stage of International Application No. PCT/EP2020/074126, filed Aug. 28, 2020, and claims priority to European Patent Application No. 19194343.0, filed Aug. 29, 2019.

SUMMARY OF THE INVENTION

The present invention relates to a composition comprising Bacilli and *Bacillus paralicheniformis* with increased growth rates and higher biomass yields at different temperatures, to its use, to a process for its preparation, to the use of Bacilli and *Bacillus paralicheniformis* with increased growth rates and higher biomass yields at different temperatures for controlling, combating and/or conferring specific resistance to plant pests. Particularly, the invention relates to strains of Bacilli and *B. paralicheniformis* with altered functionality of the proteins encoded by one or more of the genes BioF and HrcA.

The inventors of present invention have generated strains that show increased growth rates and higher biomass yields at a range of different temperatures.

Further, selected new strains of present invention is shown to induce a slight improvement in plant growth experiments, as compared to the original strain in the model plant organism *Arabidopsis thaliana.*

Genotypic variations associated with the phenotypic changes are described. Derivative strains have been tested in plant experimental systems and proven to promote increased plant growth as compared to the original strain. Further, two distinct mechanisms explaining the impact of the genetic modifications disclosed and discussed herein.

FIELD OF THE INVENTION

In the current context of a modern and ecologic society, which is concerned with preserving the environment, biological control is considered an attractive alternative or supplement to conventional methods of control. Biological control is the use of one organism (predator, parasite or pathogen) that attacks another organism which is causing economic damage to crops. This is a very common strategy in agroecological systems, as well as in conventional agriculture which relies on the Integrated Pest Management (IPM).

Although the biological control brings positive effects in the reduction or withdrawal of pesticide use and improving farmers' income, an analysis of the set of experiments worldwide, shows that the results are still concentrated in only a few crops and in select geographies with climates supporting the growth rates of Bacilli and in particular plant growth-promoting rhizobacteria as *B. paralicheniformis.* There is still much to develop in areas of control of pests and diseases.

There has been a great emphasis on research on biological control with the use of bacteria colonizing the roots of plants, called rhizobacteria. The beneficial rhizobacteria for promoting growth and/or acting in the biological control of plant pathogenic bacteria are called plant growth-promoting rhizobacteria or PGPR.

One of the key factors for successful biological control by PGPR is successful colonization of the habitat e.g. by growth rates and biomass. Hence successful biofilm formation may increase the protective effect of the PG PR.

In summary, cold adapted derivative *B. paralicheniformis* DSM33110 strains were generated following an adaptive laboratory evolution campaign. 14 improved derivatives were selected, and their genomes sequenced to identify the acquired genotypic changes. Derivative strains were characterized physiologically and tested for performance in plant growth experiments. Based on results herein we propose mechanisms to explain the observed phenotypic differences with the parental strain. In addition, these evolution experiments have contributed with a new *Bacillus* strain showing improved properties in plant growth promotion.

STATE OF THE ART

The pressure of society to replace the chemicals with environmentally acceptable products or ecological techniques has encouraged the search for alternative methods to promote plant health. In this context, biological control has been considered one of the alternatives within an integrated approach, in which one seeks to ensure sustainable development of agriculture.

The risks to humans and environments presented by using synthetic pesticides emphasize the need for tools such as biological control in optimizing sustainable agricultural systems.

Based on the idea that improved growth rates and biomass formation at different temperatures may improve the bioprotective effect of Bacilli, the inventors of present invention have selected derivative strains of Bacilli that show an increase in growth rates and biomass formation at different temperatures.

To the best of our knowledge specific genetic features linked to increased growth rates and biomass formation at different temperatures and associated mode of actions have never been described for Bacilli and in particular not for *B. paralicheniformis* strains.

3           4

μmax values reached in MSgg medium at 21° C. B. μmax values reached in MS-Rex at 21° C.

Figure 4:
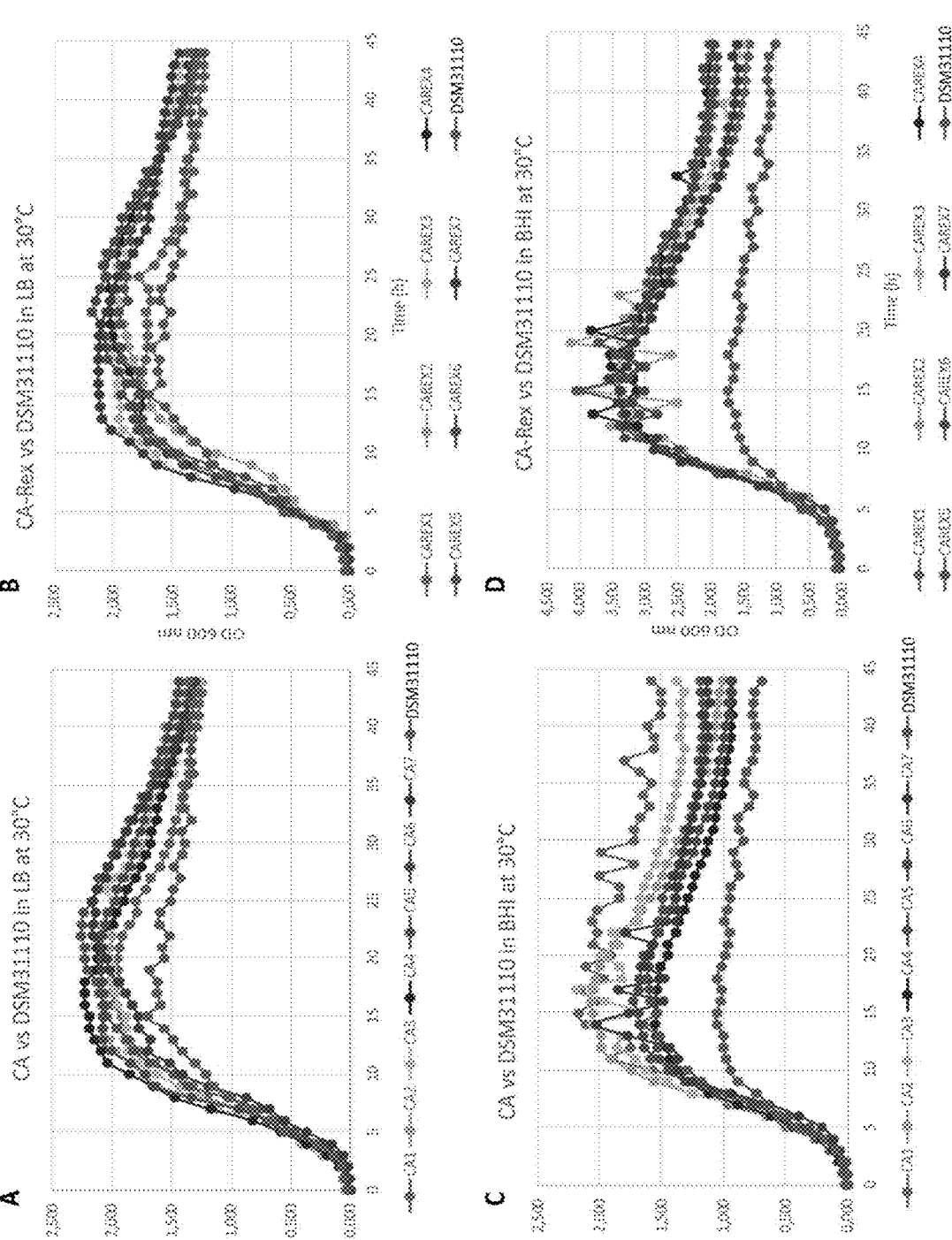

FIG. 4—Growth profiles for cold adapted derivatives in different growth media at 30° C. temperature. Growth profiles for selected cold adapted derivatives vs parental strain DSM33110. (A-B) Cold adapted derivatives were grown in LB medium at 30° C. and compared with the parental strain DSM33110. (C-D) Cold adapted derivatives were grown in BHI medium at 30° C. and compared with the parental strain DSM33110. X axes correspond to time scale of the experiment in hours. Maximum yields reached by the different strains was determined. A-C panels correspond to derivatives evolved in MSgg growth medium. B-D panels correspond to derivatives evolved in MS-Rex growth medium.

Figure 5:
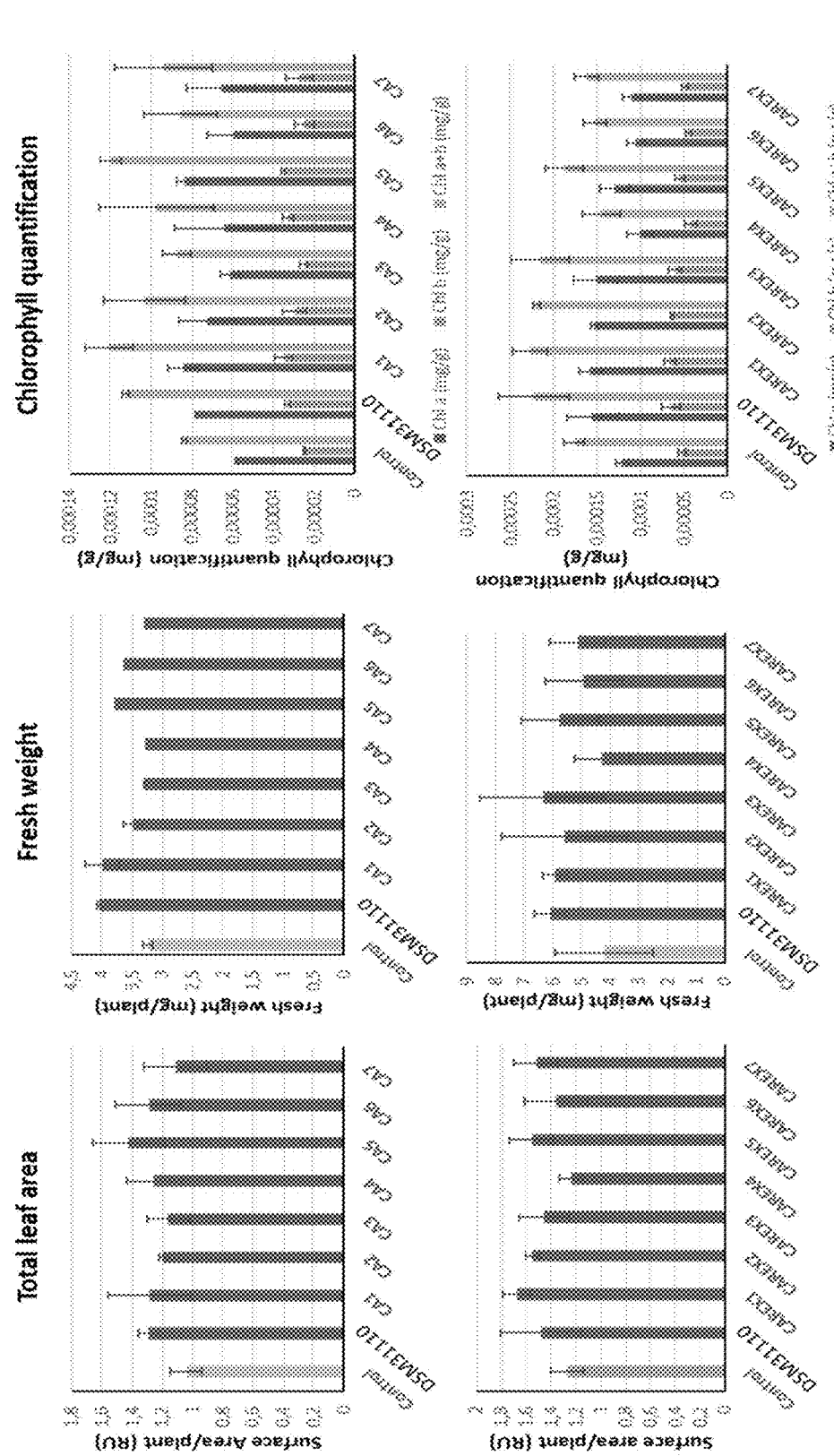

FIG. 5—Plant growth promotion experiments. Plant growth and fitness promotion quantification results from DSM33110 and 14 cold-adapted improved derivative strains CA1-CA7, and CAREX1-CAREX7 corresponding to CHCC32528-CHCC32529-CHCC36494-CHCC36497, and CHCC36751-36757, respectively. Results correspond to experiments done in an in vitro agar system. Left panel corresponds to the total leaf area measurements average calculated per plant (48 plants per strain). Central panel corresponds to the average fresh weight per plant. Right panel corresponds to chlorophyll quantification results normalized by fresh weight. Error bars correspond to standard deviation between samples.

Figure 6:
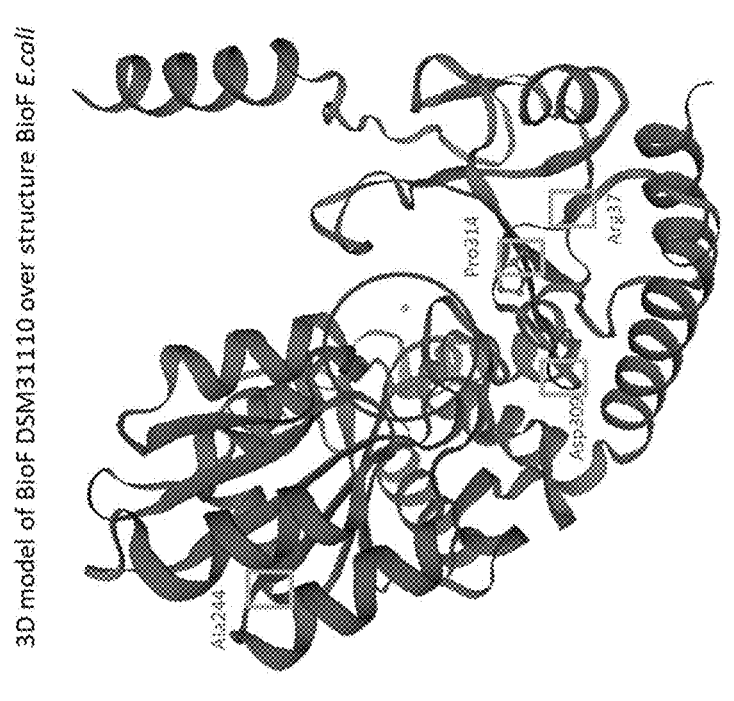

FIG. 6—A. Primary amino acid sequence alignment of BioF homologues (*E. coli* K12, *B. subtilis* 168 and *B. paralicheniformis* DSM33110, as indicated). Positions labelled with asterisks correspond to residues were identified SNPs result in an amino acid change. Squared-labelled positions correspond to catalytic residues. B. 3D structural model of BioF$_{DSM33110}$ protein. Red-circle labels the position of the catalytic residues. Green boxes correspond to position of amino acid changes identified.

Figure 7:
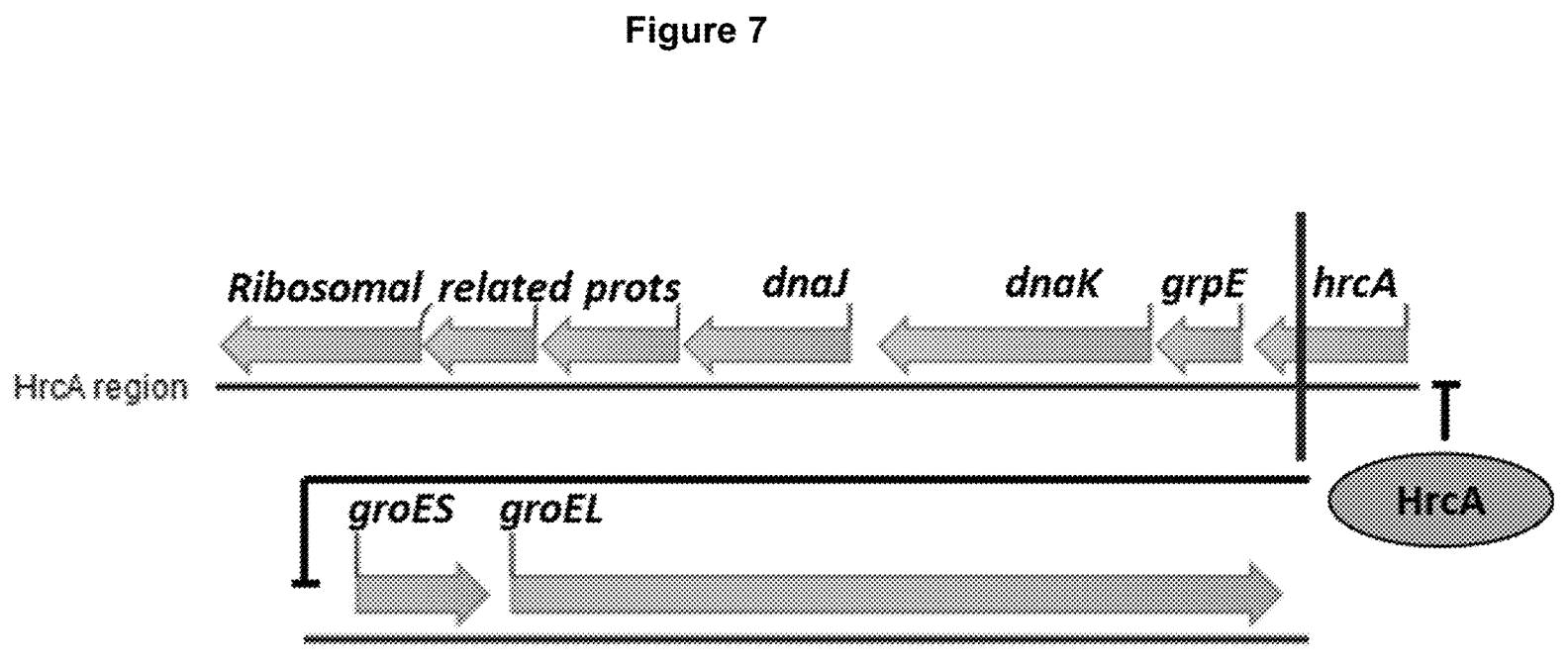

FIG. 7—Scheme representing the HrcA regulon described in *B. subtilis*. HrcA acts as transcriptional repressor of two operons, the heptacistronic dnaK operon (hrcA-grpE-dnaK-dnaJ-3xorfs), and the bicistronic groE (groES-groEL). Analysis or the homologous genomic regions present in DSM33110 confirm conservation of these operons' organization.

Figure 8:
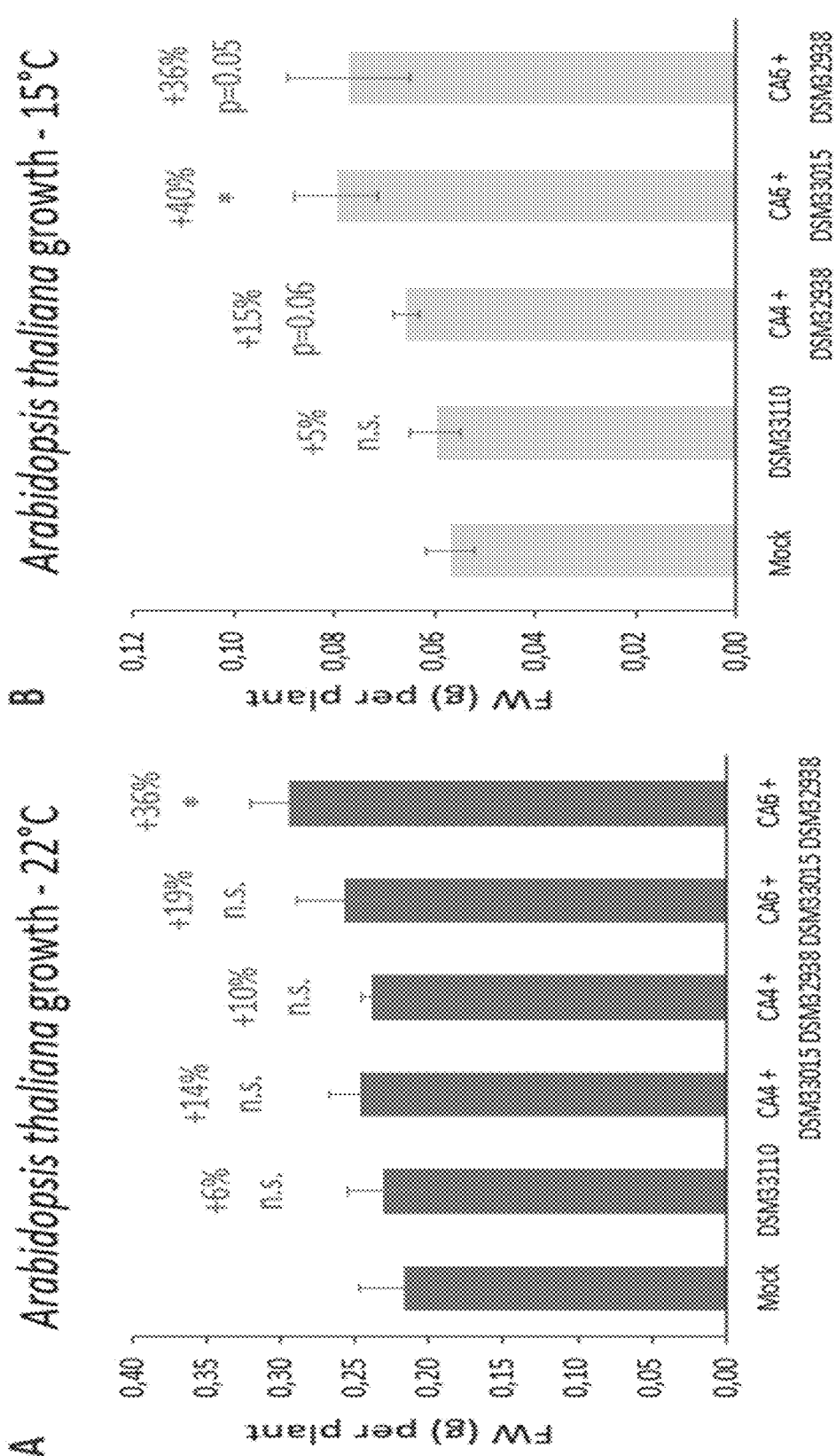

FIG. 8. Plant growth promotion by cold adapted derivatives compared in *A. thaliana* grown in potting soil. Plant growth and fitness promotion quantification results from parental strain DSM33110 and 2 cold adapted improved derivative strains (CA4 and CA6 corresponding to CHCC36494-CHCC36496, respectively). A-B. Plant growth and fitness promotion quantification results from parental strain (DSM33110) and two combinations of cold adapted derivatives CA4 and CA6 with *B. subtilis* strains DSM33015 and DSM32938, respectively. *A. thaliana* seedlings pre-grown in potting soil for 7 days were inoculated by root dipping on bacterial cultures resuspended in 10 mM MgSO$_4$ buffer (OD$_{600}$ 0.01). Plantlets were allowed to grow for 14 additional days before data collection. Error bars correspond to standard deviation between replicates and statistical significance was determined by performing a t-test (p<0.05) assuming equal variance in the two samples. A. Plant growth experiments were grown in plant growth chamber at 22° C. B. Plant growth experiments were grown in plant growth chamber at 15° C.

DETAILED DESCRIPTION OF THE INVENTION

Rhizobacteria

The soils are home to a complex biological community, of which micro-organisms, prokaryotes and eukaryotes form a majority, both in number and in diversity. Some prokaryotes have ecological niches as the rhizosphere, and/or the rhizoplane of plants, where they multiply, survive and protect themselves from the rest of the antagonistic action of soil microflora. These organisms have been generically called rhizobacteria.

In association with plants, rhizobacteria may have a deleterious effect, no effect or a beneficial effect. Those who exercise a beneficial effect—growth promotion and biological control of disease—are called PGPR ("Plant Growth-Promoting Rhizobacteria). It is estimated that only 1% to 2% of rhizobacteria have some beneficial effect for the plant with which they are associated.

PGPR as Biocontrol Agents

PGPR have been used for biological control of plant diseases and thereby increase the productivity of crops. How and why this biological control is exercised, is still a topic that needs complementary studies.

In some situations, it is possible that biological control occurs by direct antagonism exerted by PGPR against the pathogen, with involvement of the known mechanisms of antibiosis: production of antimicrobial substances, direct parasitism, competition for nutrients and ecological niches.

Research has shown that certain PGPR appear to act as elicitor of ISR (induced systemic resistance), in the sense that the plant becomes systemically protected against more than one pathogen, unlike the classical biological control, which aims to implement the control more specifically.

A significant parameter affecting the PGPR ability to infect and colonize the plant surface is the ability of the PGPR to grow under the conditions to which it is exposed. The inventors of present disclosure therefore seek to improve the growth rates and biomass formation at different, and most preferably decreased temperatures and thereby improve the plant growth promoting capabilities the Bacilli disclosed herein.

The Rhizosphere Environment

One of the most convenient methods of introducing a rhizobacteria in the root environment is through the application on the seeds before sowing. The process of seed germination releases carbohydrates and amino acids in abundance in the form of seed exudates. Thus, these organisms introduced with the seeds in the soil utilize exudates as a source of nutrition and colonize the roots as they emerge. Rhizobacteria isolates that have greater ability to utilize root exudates of seeds at different temperatures may have selective advantage in colonization of the roots.

PGPR of the genus *Bacillus* have been associated with nematode control. Sikora, R. A. (Interrelationship between plant health promoting rhizobacteria, plant parasitic nematodes and soil microorganisms. Medicine Faculty Landbouww Rijksuniv Gent, Landbouww, v. 53, n. 2b, p. 867-878, 1988) observed reductions in infection of *Meloidogyne arenaria, M. incognita* and *Rotylenchulus reniformis* around 60-65% with treatment of seeds of various crops with a strain of *Bacillus.*

Advantages of Rhizobacteria for Commercial Application

The rhizobacteria have several advantages over chemical pesticides or even on other biological control agents: they are easy to mass-produce, they are easy to store and are adaptable to the formulation technology.

The rhizobacteria can be applied by treating the substrate, immersing the seedling root systems in bacterial suspensions, watering the plant with bacterial suspension by dipping/coating the seeds in suspension of rhizobacteria or by applying PGPR with the pelleting of seeds.

Bacteria of the Genus *Bacillus*

The *Bacillus* species are Gram-positive bacteria characterized by having thick cell walls and the absence of outer membranes, which differs from the Gram-negative bacteria. Much of the cell wall of Gram-positive bacteria is composed of peptidoglycan.

Gram-positive species are divided into groups according to their morphological and biochemical characteristics. The genus *Bacillus* is belonging to the group of sporulating bacteria. Bacterial spores are one of the most resilient cell types; they resist many environmental changes, withstand dry heat and certain chemical disinfectants and may persist for years on dry land.

The beneficial effect of Bacilli such as e.g. *B. paralicheniformis*, when applied near the seed or the soil, may not be solely due to the antagonism afforded to pathogens. The PGPR has a positive influence on germination, development and crop yield due also to the production of substances which promote growth and improvement in plant nutrition by solubilization of phosphorus.

In the context of the present invention, a biofertilizer is a mixture of living microorganisms that when applied to seeds, plants or soil, promote the increase of nutrient supply, such as $NH_4^+$, $SO_4^{2-}$, $K^+$ or $PO_4^{3-}$ (Vessey, 2003).

In the context of the present invention, a plant biostimulant is any substance or microorganism applied to plants with the aim to enhance nutrition efficiency, abiotic stress tolerance and/or crop quality traits, regardless of its nutrients content. By extension, plant biostimulants also designate commercial products containing mixtures of such substances and/or microorganisms (du Jardin, 2015).

In the context of the present invention, plant growth promoting agent or plant growth promoting microorganism is a microorganism with the ability to colonize roots and/or inner plant tissues and promote plant growth and health by either acting as a biofertilizer, biostimulant or via biological control of plant disease. Said agent or microorganism is a soil and rhizosphere-inhabiting microorganism that can colonize plant roots in significant numbers ($10^5$-$10^7$ CFU per gram of fresh root) and influence plant growth in a positive manner (Spaepen et al. 2009; Antoun and Prevost 2005).

Thus, the first aspect of the invention relates to the herein described novel strains or mutants thereof.

The composition of the present invention may, besides the active components, contain agrochemical acceptable excipients and/or vehicles thereof. The composition of the invention further comprises agrochemically acceptable carriers, vehicles and/or adjuvants.

Among the main crops of plants are sugar cane, coffee, soybeans, cotton, corn, potatoes, tomatoes, tobacco, banana, rice, wheat, avocado, pineapple, squash, cacao, coconut, oats, onion, lettuce, beet, carrot, cassava, beans, sunflower, pepper, turnip, apple, strawberry, okra, radish and onion.

For fruticulture: citrus, grape, guava, papaya, fig, peach, plum and nespereira are of particular relevance and with regard to horticulture: eggplant and cruciferous.

For floriculture: rose, chrysanthemum, lisianthus, gerbera, amaryllis, begonia and celosia.

The composition of present invention may be coated on the plant seed and can include an amount of *Bacillus*, such as e.g. *B. paralicheniformis* spores from about $1.0 \times 10^2$ CFU/seed to about $1.0 \times 10^9$ CFU/seed.

The plant seed can include, but is not limited to, the seed of monocots, dicots, Cereals, Corn, Sweet Corn, Popcorn, Seed Corn, Silage Corn, Field Corn, Rice, Wheat, Barley, Sorghum, *Brassica* Vegetables, Broccoli, Cabbage, Cauliflower, Brussels Sprouts, Collards, Kale, Mustard Greens, Kohlrabi, Bulb Vegetables, Onion, Garlic, Shallots, Fruiting Vegetables, Pepper, Tomato, Eggplant, Ground Cherry, Tomatillo, Okra, Grape, Herbs/Spices, Cucurbit Vegetables, Cucumber, Cantaloupe, Melon, Muskmelon, Squash, Watermelon, Pumpkin, Eggplant, Leafy Vegetables, Lettuce, Celery, Spinach, Parsley, Radicchio, Legumes/Vegetables (succulent and dried beans and peas), Beans, Green beans, Snap beans, Shell beans, Soybeans, Dry Beans, Garbanzo beans, Lima beans, Peas, Chick peas, Split peas, Lentils, Oil Seed Crops, Canola, Castor, Cotton, Flax, Peanut, Rapeseed, Safflower, Sesame, Sunflower, Soybean, Root/Tuber and Corm Vegetables, Carrot, Potato, Sweet Potato, Beets, Ginger, Horseradish, Radish, Ginseng, Turnip, sugarcane, sugarbeet, Grass, or Turf grass.

Further, the plant seed can include seed of a drybean, a corn, a wheat, a soybean, a canola, a rice, a cucumber, a pepper, a tomato, a squash, a cotton, a grass, and a turf grass.

In an alternative embodiment, the *Bacillus* or composition of present invention may be added to: soil or growth medium surrounding the plant; soil or growth medium before sowing seed of the plant in the soil or growth medium; or soil or growth medium before planting the plant, the plant cutting, the plant graft, or the plant callus tissue in the soil or growth medium.

In one or more embodiments, the plant can include soybean, bean, snap bean, wheat, cotton, corn, pepper, tomato, potato, cassava, grape, strawberry, banana, peanut, squash, pumpkin, eggplant, and cucumber.

In the compositions and methods of the present invention, the pathogenic infection can be caused by a wide variety of plant pathogens including, for example, but not limited to, a plant fungal pathogen, a plant bacterial pathogen, a rust fungus, a *Botrytis* spp., a *Botrytis cinerea*, a *Botrytis squamosa*, an *Erwinia* spp., an *Erwinia carotovora*, an *Erwinia amylovora*, a *Dickeya* spp., a *Dickeya dadantii*, a *Dickeya solani*, an *Agrobacterium* spp., a *Agrobacterium tumefaciens*, a *Xanthomonas* spp., a *Xanthomonas axonopodis*, a *Xanthomonas campestris* pv. *carotae*, a *Xanthomonas pruni*, a *Xanthomonas arboricola*, a *Xanthomonas oryzae* pv. *oryzae*, a *Xylella* spp., a *Xylella fastidiosa*, a *Candidatus* spp., a *Candidatus liberibacter*, a *Fusarium* spp., a *Fusarium culmorum*, a *Fusarium graminearum*, a *Fusarium oxysporum*, a *Fusarium oxysporum* f. sp. *Cubense*, a *Fusarium oxysporum* f. sp. *Lycopersici*, a *Fusarium virguliforme*, a *Sclerotinia* spp., a *Sclerotinia sclerotiorum*, a *Sclerotinia minor*, *Sclerotinia homeocarpa*, a *Cercospora/Cercosporidium* spp., an *Uncinula* spp., an *Uncinula necator* (Powdery Mildew), a *Podosphaera* spp. (Powdery Mildew), a *Podosphaera leucotricha*, a *Podosphaera clandestine*, a *Phomopsis* spp., a *Phomopsis viticola*, an *Alternaria* spp., an *Alternaria tenuissima*, an *Alternaria porri*, an *Alternaria alternate*, an *Alternaria solani*, an *Alternaria tenuis*, a *Pseudomonas* spp., a *Pseudomonas syringae* pv. Tomato, a *Phytophthora* spp., a *Phytophthora infestans*, a *Phytophthora parasitica*, a *Phytophthora sojae*, a *Phytophthora capsici*, a *Phytophthora cinnamon*, a *Phytophthora fragariae*, a *Phytophthora* spp., a *Phytophthora ramorum*, a *Phytophthora palmivara*, a *Phytophthora nicotianae*, a *Phakopsora* spp., a *Phakopsora pachyrhizi*, a *Phakopsora meibomiae* an *Aspergillus* spp., an *Aspergillus flavus*, an *Aspergillus niger*, a *Uromyces* spp., a *Uromyces appendiculatus*, a *Cladosporium* spp., a *Cladosporium herbarum*, a *Rhizopus* spp., a *Rhizopus arrhizus*, a *Penicillium* spp., a *Rhizoctonia* spp., a *Rhizoctonia solani*, a *Rhizoctonia zeae*, a *Rhizoctonia oryzae*, a *Rhizoctonia caritae*, a *Rhizoctonia cerealis*, a

*Rhizoctonia crocorum,* a *Rhizoctonia fragariae,* a *Rhizoctonia ramicola,* a *Rhizoctonia rubi,* a *Rhizoctonia leguminicola,* a *Macrophomina phaseolina,* a *Magnaorthe oryzae,* a *Mycosphaerella* spp., *Mycosphaerella graminocola,* a *Mycosphaerella fijiensis* (Black sigatoga), a *Mycosphaerella pomi,* a *Mycosphaerella citri,* a *Magnaporthe* spp., a *Magnaporthe grisea,* a *Monilinia* spp., a *Monilinia fruticola,* a *Monilinia vacciniicorymbosi,* a *Monilinia laxa,* a *Colletotrichum* spp., a *Colletotrichum gloeosporiodes,* a *Colletotrichum acutatum,* a *Colletotrichum Candidum,* a *Diaporthe* spp., a *Diaporthe citri,* a *Corynespora* spp., a *Corynespora Cassiicola,* a *Gymnosporangium* spp., a *Gymnosporangium juniperi-virginianae,* a *Schizothyrium* spp., a *Schizothyrium pomi,* a *Gloeodes* spp., a *Gloeodes pomigena,* a *Botryosphaeria* spp., a *Botryosphaeria dothidea,* a *Neofabraea* spp., a *Wilsonomyces* spp., a *Wilsonomyces carpophilus,* a *Sphaerotheca* spp., a *Sphaerotheca macularis,* a *Sphaerotheca pannosa,* a *Erysiphe* spp., a *Stagonospora* spp., a *Stagonospora nodorum,* a *Pythium* spp., a *Pythium ultimum,* a *Pythium aphanidermatum,* a *Pythium irregularum,* a *Pythium ulosum,* a *Pythium lutriarium,* a *Pythium sylvatium,* a *Venturia* spp, a *Venturia inaequalis,* a *Verticillium* spp., a *Ustilago* spp., a *Ustilago nuda,* a *Ustilago maydis,* a *Ustilago scitaminea,* a *Claviceps* spp., a *Claviceps puprrea,* a *Tilletia* spp., a *Tilletia tritici,* a *Tilletia laevis,* a *Tilletia horrid,* a *Tilletia controversa,* a *Phoma* spp., a *Phoma glycinicola,* a *Phoma exigua,* a *Phoma lingam,* a *Cocliobolus sativus,* a *Gaeumanomyces gaminis,* a *Colleototricum* spp., a *Rhychosporium* spp., *Rhychosporium secalis,* a *Biopolaris* spp., a *Helminthosporium* spp., a *Helminthosporium secalis,* a *Helminthosporium maydis,* a *Helminthosporium solai,* and a *Helminthosporium tritici-repentis,* or combinations thereof. In some embodiments, the pathogenic infection can be caused by one or a combination of: Soybean rust fungi (*Phakopsora pachyrhizi, Phakopsora meibomiae*) and the plant comprises soybean; *Botrytis cinerea* (*Botrytis* Blight) and the plant comprises grape; *Botrytis cinerea* (*Botrytis* Blight) and the plant comprises strawberry; *Botrytis cinerea* (*Botrytis* Blight) and the plant comprises tomato; *Alternaria* spp. (e.g. *A. solani*) and the plant comprises tomato; *Alternaria* spp. (e.g. *A. solani*) and the plant comprises potato; Bean Rust (*Uromyces appendiculatus*) and the plant comprises common bean; *Microsphaera diffusa* (Soybean Powdery Mildew) and the plant comprises soybean; *Mycosphaerella fijiensis* (Black sigatoga) or *Fusarium oxysporum* f. sp. *cubense* (Panama disease) and the plant comprises banana; *Xanthomonas* spp. or *Xanthomonas oryzae* pv. *oryzae* and the plant comprises rice; *Xanthomonas axonopodis* and the plant comprises cassava; *Xanthomonas campestris* and the plant comprises tomato; *Botrytis cinerea* (Pepper *Botrytis* Blight) and the plant comprises pepper; Powdery mildew and the plant comprises a cucurbit; *Sclerotinia sclerotiorum* (white mold) and the plant comprises snap bean; *Sclerotinia sclerotiorum* (white mold) and the plant comprises potato; *Sclerotinia homeocarpa* (dollar spot) and the plant comprises turfgrass; Southern White Mold and the plant comprises peanut; Leaf spot (*Cercospora/Cercosporidium*) and the plant comprises peanut; *Fusarium graminearum* (Wheat Head Scab) and the plant comprises wheat; *Mycosphaerella graminicola* (*Septoria tritici* blotch) and the plant comprises wheat; *Stagonospora nodorum* (glume blotch and *Septoria nodorum* blotch), and the plant compromises wheat; *Erwinia amylovora,* and the plant compromises apple, pear and other pome fruits; *Venturia inaequalis,* and the plant compromises apple, pear and other pome fruits; or *Rhizoctonia solani* and the plant comprises wheat, rice, turfgrass, soybean, corn, legumes and vegetable crops. The compositions including the bacilli as described herein strain can be in the form of a liquid, an oil dispersion, a dust, a dry wettable powder, a spreadable granule, or a dry wettable granule. More specifically the composition may for example be an emulsion concentrate (EC), a suspension concentrate (SC), a suspo-emulsion (SE), a capsule suspension (CS), a water dispersible granule (WG), an emulsifiable granule (EG), a water in oil emulsion (EO), an oil in water emulsion (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a dispersible concentrate (DC), a wettable powder (WP) or any technically feasible formulation in combination with agriculturally acceptable adjuvants.

Hence, the present invention relates to a composition comprising *Bacillus paralicheniformis* DSM 33238, DSM 33239, DSM 33240, DSM 33241, DSM 33242, DSM 33243, DSM 33244 or mutants thereof or a mutant thereof, and to a kit comprising the composition, or prepared by the process of preparing the composition, as well as instructions and a suitable recipient. Accordingly, the present invention also relates to a process for preparing a composition comprising *Bacillus paralicheniformis* DSM 33238, DSM 33239, DSM 33240, DSM 33241, DSM 33242, DSM 33243, DSM 33244, or a mutant thereof together with agrochemically acceptable carriers, vehicles and/or adjuvants, and use of said composition for controlling, combating and/or conferring specific resistance to phytonematodes are also given.

In addition, the invention refers to the use of effective amounts of *Bacillus paralicheniformis* DSM 33238, DSM 33239, DSM 33240, DSM 33241, DSM 33242, DSM 33243, DSM 33244 or a mutant thereof, in the manufacture of an agrochemical composition with plant growth promoting effect in a plant culture, as well as processes for promoting plant health.

In a preferred aspect the invention relates to a *Bacillus* having a mutation in the bioF gene, wherein the mutation changes the enzyme kinetics of the protein encoded by bioF, when compared to the parental strain of the *Bacillus* having a mutation in the bioF gene.

In yet a preferred aspect the invention relates to a *Bacillus* having a mutation in the hrcA gene, wherein the mutation renders the protein encoded by hrcA dysfunctional such loss of function, when compared to its parental strain.

Further, the present invention relates to the following aspects:

Aspect 1. A *Bacillus* having mutation in the bioF and/or hrcA gene.

Aspect 2. A *Bacillus* having a mutation in the hrcA and/or bioF gene when compared to the corresponding ortholog genes of hrcA and bioF in *B. paralicheniformis* deposited as DSM33110.

Aspect 3. A *Bacillus* having a mutation in the hrcA gene when compared to SEQ ID NO:1 and/or a mutation in the bioF gene when compared to the SEQ ID NO:3.

Aspect 4. A *Bacillus* selected from a list consisting of the strains deposited at Deutsche Sammlung von Mikroorganismen and Zellkulturen with accession No's. DSM 33238, DSM 33239, DSM 33240, DSM 33241, DSM 33242, DSM 33243, DSM 33244.

Aspect 5. A *Bacillus* according to any of the preceding aspects, wherein the closest ortholog of the bioF gene of said *Bacillus* share less than 100% such as e.g. less than 99%, less than 98% sequence identity with SEQ ID NO:1.

Aspect 6. A *Bacillus* according to any of the preceding aspects, wherein the closest ortholog of the bioF gene of said *Bacillus* share at least 95% such as e.g. at least 96%, at least 97, at least 98, at least 99% sequence identity with SEQ ID NO:1.

Aspect 7. A *Bacillus* according to any of the preceding aspects, wherein the closest ortholog of the hrcA gene of said *B. paralicheniformis* share less than 100% such as e.g. less than 99%, less than 98% sequence identity with SEQ ID NO:3.

Aspect 8. A *Bacillus* according to any of the preceding aspects, wherein the closest ortholog of the hrcA gene of said *Bacillus* share at least 95% such as e.g. at least 96%, at least 97 sequence identity with SEQ ID NO:3.

Aspect 9. A *Bacillus* according to any of the preceding aspects, wherein the mutation is a deletion, substitution or insertion.

Aspect 10. A *Bacillus* according to any of the preceding aspects, wherein the mutation causes a frameshift, introduces a stop codon or impacts the kinetics of the encoded protein.

Aspect 11. A *Bacillus* according to any of the preceding aspects, wherein the protein encoded by one or more of the genes hrcA and/or bioF or one or more of their closest orthologs is structurally impacted by the mutation.

Aspect 12. A *Bacillus* according to any of the preceding aspects, wherein the genome of the strain is at least 99%, such as e.g. at least 99.5%, such as e.g. at least 99.8%, such as e.g. at least 99.9% identical to the genome of the strain deposited at Deutsche Sammlung von Mikroorganismen und Zellkulturen with accession No. DSM33110.

Aspect 13. A *Bacillus* according to any of the preceding aspects, wherein the *Bacillus* is selected from: *Bacillus licheniformis, Bacillus amyloliquefaciens, Bacillus paralicheniformis, Bacillus cereus, Bacillus velenzensis, Bacillus megaterium.*

Aspect 14. A *Bacillus* according to any of the preceding aspects, wherein the strain is derived from the strain deposited at Deutsche Sammlung von Mikroorganismen und Zellkulturen with accession No. DSM33110 or a strain sharing pheno- or genotypical characteristics with the strain deposited at Deutsche Sammlung von Mikroorganismen und Zellkulturen with accession No. DSM33110.

Aspect 15. A *Bacillus* according to any of the preceding aspects wherein the *Bacillus* has the pheno- or genotypical characteristics of one or more of the *Bacillus paralicheniformis* strains deposited at Deutsche Sammlung von Mikroorganismen und Zellkulturen with accession No's. DSM 33238, DSM 33239, DSM 33240, DSM 33241, DSM 33242, DSM 33243, DSM 33244.

Aspect 16. A *Bacillus* according to any of the preceding aspects showing increased growth rates when compared with the *Bacillus paralicheniformis* deposited at Deutsche Sammlung von Mikroorganismen und Zellkulturen with accession no. DSM33110, when grown at 21° C. in MSgg and/or MS-rex medium.

Aspect 17. A *Bacillus* according to aspect 16 wherein the growth rate is determined as described in Example 2 herein.

Aspect 18. A *Bacillus* according to any of aspects 16 or 17 where the growth rate exceeds the growth rate of the parental strain by at least 20%, such as at least 40%, such as at least 60%, such as at least 80%, such as at least 100%.

Aspect 19. A composition comprising a *Bacillus* according to any of the preceding aspects.

Aspect 20. A composition comprising a *Bacillus* according to any of the preceding aspects and agrochemically acceptable excipients and/or carriers thereof.

Aspect 21. The composition of any of aspects 19 or 20, further comprising one or a combination of a microbial, a biological, or a chemical insecticide, fungicide, nematicide, bactericide, herbicide, plant extract, plant growth regulator, or fertilizer present in an amount suitable to benefit plant growth and/or to confer protection against a pathogenic infection in a susceptible plant, a carrier, a surfactant, a dispersant, or a yeast extract.

Aspect 22. Use of a composition according to any of aspects 19 to 21 or a *Bacillus* according to any of aspects 1 to 18 as a biostimulant and/or bionematicide.

Aspect 23. Use of a composition, according to any of aspects 19 to 21, or a *Bacillus* according to any of aspects 1 to 18 for controlling, combating and/or conferring specific resistance to phytonematodes.

Aspect 24. Use according to any of aspects 22 or 23, wherein the phytonematodes are selected from the group consisting of *Meloidogyne, Pratylenchus, Heterodera, Globodera, Ditylenchus, Tylenchulus, Xiphinema, Radopholus, Rotylenchulus, Helicotylenchus* and *Belonolaimus.*

Aspect 25. Use according to any of aspects 22 to 24, wherein the phytonematode is selected from the group consisting of *Meloidogyne incognita, Meloidogyne javanica, Meloidogyne exigua, Meloidogyne paranaensis, Heterordera glycines* and *Pratylenchus zeae.*

Aspect 26. Use according to any of aspects 22 to 25 wherein the composition according to any of aspects 19 to 21 or the *Bacillus* according to any of aspects 1 to 18 is applied on a plant, a seed or in the habitat of a plant Aspect 27. Use according to aspect 26 wherein the plant is selected from the group consisting of corn, rice, sugar cane, soybean, potato, carrot, coffee and banana.

Aspect 28. Process for conferring improved resistance to phytonematodes, comprising applying an effective amount of a *Bacillus* of any of aspects 1 to 18 or a composition according to any of aspects 19 to 21 on plants and/or their habitat.

Aspect 29. Kit, comprising the composition as defined in any one of aspects 19 to 21, instructions for use and a suitable container.

Aspect 30. A plant seed coated with a composition according to any of aspects 19 to 21 present in an amount suitable to benefit plant growth and/or to confer protection against a pathogenic infection in a susceptible plant.

Aspect 31. The plant seed of aspect 30, wherein the composition comprises an amount of spores of the *Bacillus* of any of aspects 1 to 18 from about $1.0 \times 10^2$ CFU/seed to about $1.0 \times 10^9$ CFU/seed.

Aspect 32. The plant seed of aspect 30 or 312, wherein the composition further comprises one or a combination of a microbial, a biological, or a chemical insecticide, fungicide, nematicide, bactericide, or plant growth regulator present in an amount suitable to benefit plant growth and/or to confer protection against a pathogenic infection in a susceptible plant.

Aspect 33. A *Bacillus* according to any of aspects 1 to 18 wherein BioF is encoded by the DNA sequence of SEQ ID NO:1 or amino acid sequence of SEQ ID NO: 2 or homologs thereof and/or HrcA is encoded by the DNA sequence of SEQ ID NO:3 or amino acid sequence homologs thereof.

Item 1. A *Bacillus paralicheniformis* having a mutation in the hrcA and/or bioF gene when compared to the corresponding ortholog genes of hrcA and/or bioF in *B. paralicheniformis* deposited at Deutsche Sammlung von Mikroorganismen und Zellkulturen (DSMZ) with accession no. DSM33110.

Item 2. A *Bacillus paralicheniformis* having a mutation in the hrcA and/or bioF gene when compared to the corresponding ortholog genes of hrcA encoded by SEQ ID NO: 1 and/or bioF encoded by SEQ ID NO:

3 in e.g. *B. paralicheniformis* deposited at Deutsche Sammlung von Mikroorganismen und Zellkulturen (DSMZ) as DSM33110.

Item 3. A *Bacillus paralicheniformis* according to any of items 1 or 2, wherein the *Bacillus paralicheniformis* is a mutant derived from *B. paralicheniformis* deposited as DSM33110.

Item 4. A *Bacillus paralicheniformis* deposited at Leibniz Institute DSMZ—German Collection of Microorganisms and Cell Cultures, Inhoffenstr. 7B, D-38124 Braunschweig (DSMZ) as DSM 33238, DSM 33239, DSM 33240, DSM 33241, DSM 33242, DSM 33243 or DSM 33244.

Item 5. A *Bacillus paralicheniformis* according to any of items 1 to 4 wherein the mutation in the bioF gene causes a genotypic change imposing an amino acid change from Pro314 to Ser, Ala244 to Val, Asp300 to Gly and/or Arg37 to Trp.

Item 6. A *Bacillus paralicheniformis* according to any of items 1 to 5 wherein the mutation in the hrcA gene causes a genotypic change imposing a stop codon, rendering an inactive HrcA repressor.

Item 7. A *Bacillus paralicheniformis* according to any of the preceding items showing increased maximum growth rates when compared with the *Bacillus paralicheniformis* deposited at Deutsche Sammlung von Mikroorganismen und Zellkulturen (DSMZ) with accession no. DSM33110, when grown at 21° C. in MSgg.

Item 8. A *Bacillus paralicheniformis* according to item 7 wherein the maximum growth rate is determined as described in Example 2 herein.

Item 9. A *Bacillus paralicheniformis* according to any of the preceding items wherein the growth rate of the *Bacillus paralicheniformis* strain according to any of the preceding items exceeds the growth rate of the *Bacillus paralicheniformis* deposited at Deutsche Sammlung von Mikroorganismen und Zellkulturen (DSMZ) under accession no. DSM33110 by at least 20%, such as at least 40%, such as at least 60%, such as at least 80%, such as at least 100%.

Item 10. A *Bacillus paralicheniformis* according to any of the preceding claims which when applied to a *Arabidopsis thaliana* Col-0 plants, in a gnotobiotic plant system and grown for 22° C. and/or 15° C. is able to increase the total leaf area, the fresh weight or the chlorophyll content in said *A. thaliana*.

Item 11. A composition comprising a *Bacillus paralicheniformis* according to any of the preceding items and agrochemically acceptable excipients and/or carriers thereof.

Item 12. A composition of item 11, further comprising one, or a combination of a microbial, a biological, or a chemical insecticide, fungicide, nematicide, bactericide, herbicide, plant extract, plant growth regulator, or fertilizer present in an amount suitable to benefit plant growth and/or to confer protection against a pathogenic infection in a susceptible plant, a carrier, a surfactant, a dispersant, or a yeast extract.

Item 13. Use of a composition according to any of items 11 to 12 or a *Bacillus paralicheniformis* according to any of items 1 to 9 as a biostimulant, growth promoter and/or bionematicide.

Item 14. Use according to item 13, wherein the phytonematodes are selected from the group consisting of *Meloidogyne, Pratylenchus, Heterodera, Globodera, Ditylenchus,*

*Tylenchulus, Xiphinema, Radopholus, Rotylenchulus, Helicotylenchus* and *Belonolaimus* such as e.g. *Meloidogyne incognita, Meloidogyne javanica, Meloidogyne exigua, Meloidogyne paranaensis, Heterordera glycines* and *Pratylenchus zeae*.

Item 15. Use according to any of items 13 to 14 wherein the composition according to any of items 11 to 12 or the *Bacillus licheniformis* according to any of items 1 to 10 is applied on a plant, a seed or in the habitat of a plant, such as in the soil.

Item 16. Use according to any of items 13 to 15 wherein the plant is selected from the group consisting of corn, rice, sugar cane, soybean, potato, carrot, coffee and banana.

Item 17. A plant seed coated with a composition according to any of items 11 to 12 present in an amount suitable to benefit plant growth and/or to confer protection against a pathogenic infection in a susceptible plant.

Item 18. The plant seed of item 17, wherein the composition comprises an amount of spores of the *Bacillus* of any of items 1 to 10 from about $1.0 \times 10^2$ CFU/seed to about $1.0 \times 10^9$ CFU/seed.

Item 19. The plant seed of item 18 or 18, wherein the composition further comprises one or a combination of a microbial, a biological, or a chemical insecticide, fungicide, nematicide, bactericide, or plant growth regulator present in an amount suitable to benefit plant growth and/or to confer protection against a pathogenic infection in a susceptible plant.

The illustrative examples presented below serve to better describe the present invention. However, the formulations described merely refer to some means to some embodiments of the present invention and should not be taken as limiting the scope thereof.

As used in present disclosure the strain descriptors are used interchangeably according to the table below:

| | |
|---|---|
| CHCC32528 | CA1 |
| CHCC32529 | CA2 |
| CHCC32530 | CA3 |
| CHCC36494 | CA4 |
| CHCC36495 | CA5 |
| CHCC36496 | CA6 |
| CHCC36497 | CA7 |
| CHCC36751 | CAREX1 |
| CHCC36752 | CAREX2 |
| CHCC36753 | CAREX3 |
| CHCC36754 | CAREX4 |
| CHCC36755 | CAREX5 |
| CHCC36756 | CAREX6 |
| CHCC36757 | CAREX7 |

EXAMPLES

Growth Media Compositions:

MSgg Medium (pH 7) (Filter Sterilized):

MOPS solution 1×:

100 mM morpholinepropanesulfonic acid (MOPS) (pH 7)

5 mM KH2PO4/K2HPO4

1× Trace Elements Solution:

50 µM MnCl2

1 µM ZnCl2

100 µM FeCl3

2 mM MgCl2

700 µM CaCl2)

2 µM thiamine

Amino Acid Supplements

50 µg/ml threonine, tryptophan and/or phenylalanine

Carbon Sources 0.5% glutamate 0.5% glycerol

MS-REX (pH 7) Filter Sterilized

Murashige and Skoog (MS) medium is a plant growth medium used in the laboratories for cultivation of plants or plant cell cultures. MS was supplemented with corn root exudates (1×) collected from hydroponic maize plants cultures. Root exudates had been collected in water, and liophylized to obtain a concentrate of the root exudates (×25).

MS Composition

Major Salts (Macronutrients)/1 L

Ammonium nitrate (NH4NO3) 1,650 mg/l

Calcium chloride (CaCl2·2H2O) 440 mg/l

Magnesium sulfate (MgSO4·7H2O) 370 mg/l

Monopotassium phosphate (KH2PO4) 170 mg/l

Potassium nitrate (KNO3) 1,900 mg/l.

Minor Salts (Micronutrients)/1 L

Boric acid (H3BO3) 6.2 mg/l

Cobalt chloride (CoCl2·6H2O) 0.025 mg/l

Ferrous sulfate (FeSO4·7H2O) 27.8 mg/l

Manganese(II) sulfate (MnSO4·4H2O) 22.3 mg/l

Potassium iodide (KI) 0.83 mg/l

Sodium molybdate (Na2MoO4·2H2O) 0.25 mg/l

Zinc sulfate (ZnSO4·7H2O) 8.6 mg/l

Ethylenediaminetetraacetic acid ferric sodium (NaFe-EDTA) constituting 5 ml/l of a stock solution containing 5.57 g FeSO4·7H2O and 7.45 g Nat-EDTA per litre of water.

Copper sulfate (CuSO4·5H2O) 0.025 mg/l

Vitamins and organic compounds/1 L

Myo-Inositol 100 mg/l

Nicotinic Acid 0.5 mg/l

Pyridoxine·HCl 0.5 mg/l

Thiamine·HCl 1.0 mg/l

Glycine 2 mg/l

Example 1: Adaptive Laboratory Evolution (ALE)

Figure 1:
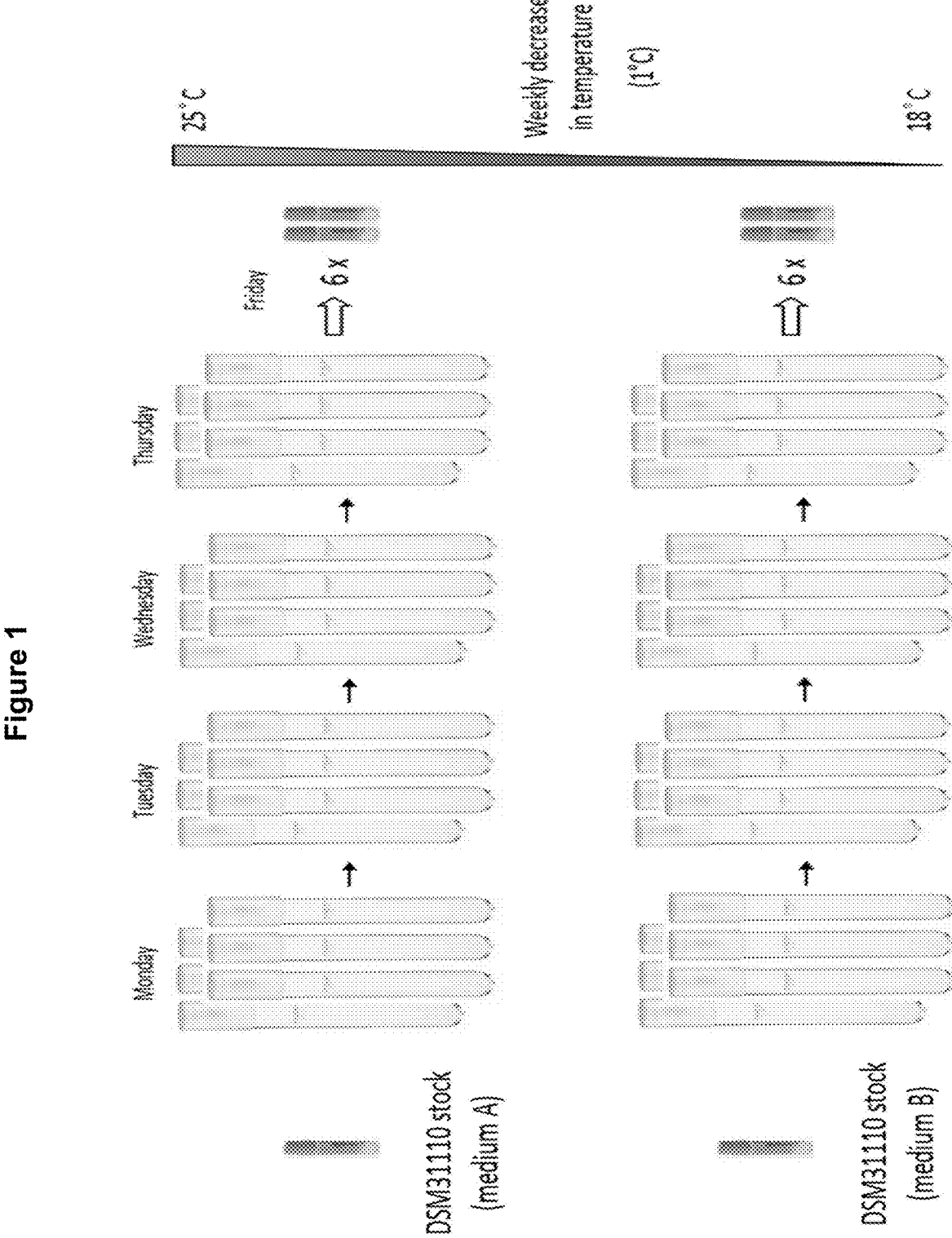
FIG. 1—ALE generation of cold adapted strains: experimental approach. A. ALE experimental approach to select for cold adapted DSM33110 derivatives was followed for 12 weeks. 5-10% dilution to fresh medium of 12 independent overnight cultures was done daily (6 independent cultures were evolved in two different growth media). OD (600 nm) measurements were taken daily and number of generations per week calculated. Samples from each tube were kept frozen as glycerol stocks weekly. Temperature was gradually decreased from 25° C. to 18° C. throughout the ALE progression. B. After 12 weeks of adaptive laboratory evolution, serial dilutions from each culture were plated, and 2×960 independent clones were selected, grown in LB broth, and kept frozen as glycerol stocks in 96-well microtiter plates. Individual clone growth profiles were compared first in a Growth Profiler 960 at 21° C. The 14 faster growers were selected and their growth patterns analyzed in different growth media and temperatures.

We performed an adaptive laboratory evolution (ALE) campaign to develop derivatives of *B. paralicheniformis* DSM33110 with improved growth rates at cold tempera-tures. Two different growth media were selected to carry on the evolution process in parallel. 12 independent cultures (6 per growth medium) were grown over-night and diluted every day to fresh medium (see FIG. 1). Initially, MSgg or MS-Rex growth media were inoculated from a stock of *Bacillus paralicheniformis* DSM33110 cell culture (OD600 1). Optical density of DSM33110 subcultures was monitored daily and subsequently diluted to fresh growth medium. Two glycerol stocks were prepared per tube weekly. One was used for inoculation of a new round of growth passages, while the second one was kept frozen. Temperature was gradually decreased from 25° C. to 18° C. throughout the 12 weeks of ALE campaign. Total number of generations reached was counted, and after 12 weeks of adaptive evolution, cultures were grown for 120-140 generations. Final samples from the evolution experiment were serially diluted and plated on LB agar plates to obtain isolated colonies. 2×960 clones were picked with a colony picker robot and grown in 96 well plates to generate individual glycerol stocks.

Example 2: Growth Rate Analysis

Figure 2:
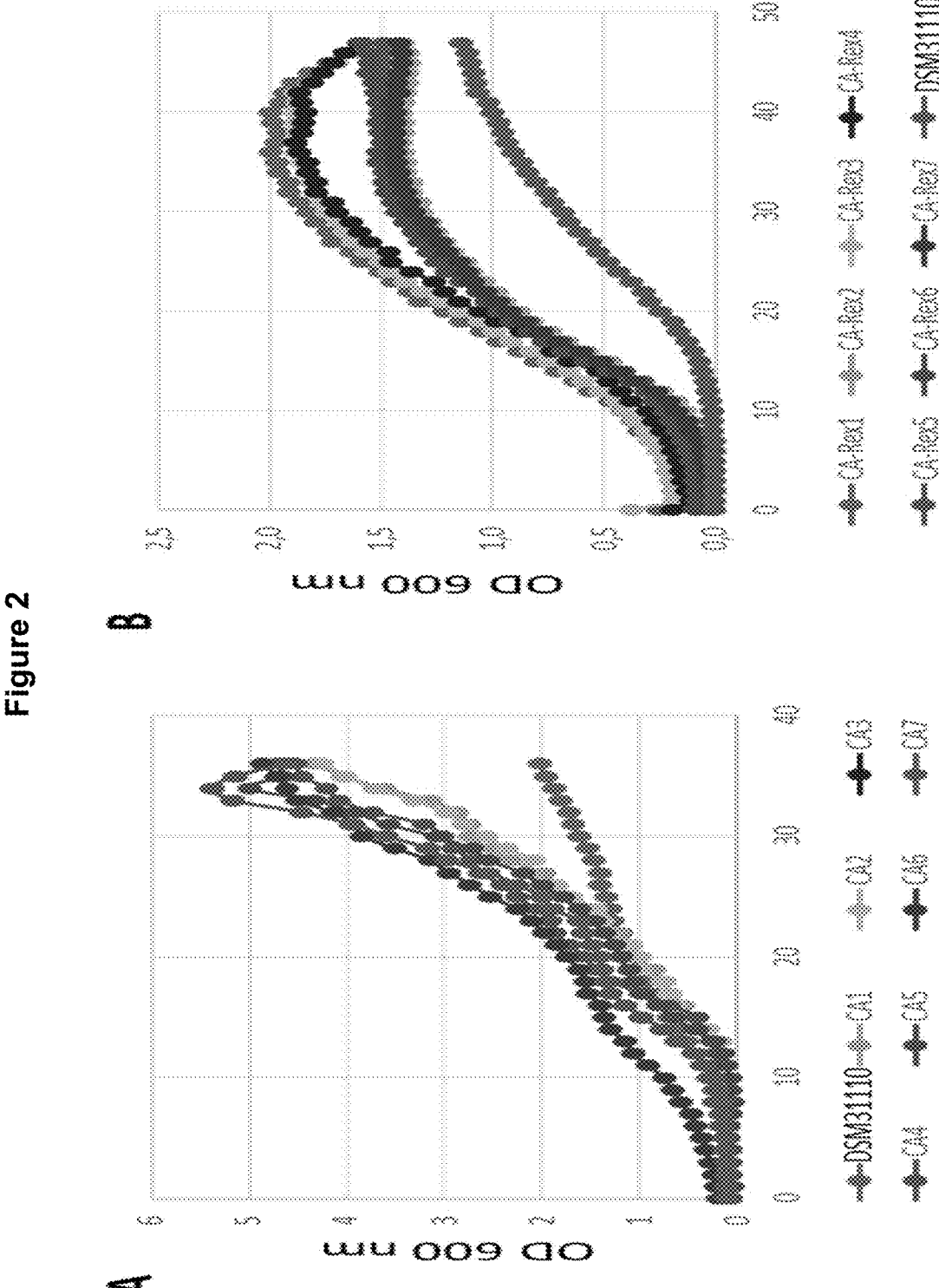
FIG. 2—Growth profiles of the selected cold adapted derivatives vs parental strain DSM33110. A. Cold adapted derivatives evolved in MSgg growth medium were grown in MSgg medium at 21° C. and compared with the parental strain DSM33110. B. Cold adapted derivatives evolved in MS-Rex growth medium were grown in MS-Rex medium at 21° C. and compared with the parental strain DSM33110. Maximum biomass yields reached by the different strains were determined.
Figure 3:
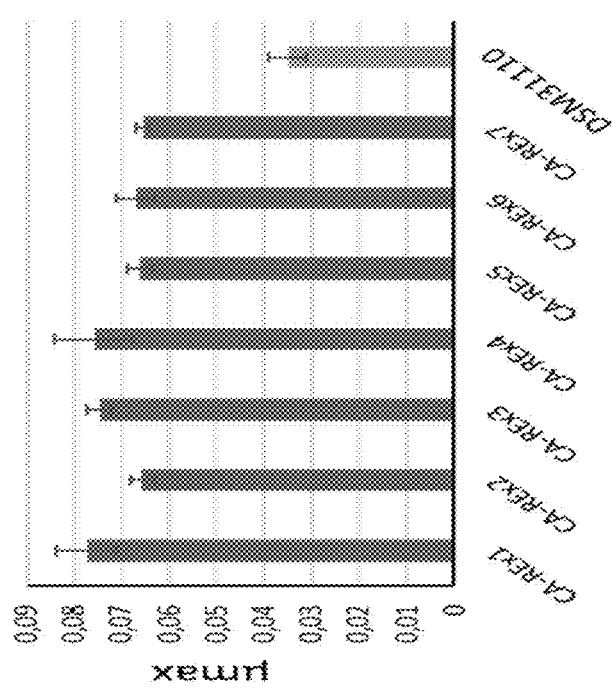
FIG. 3—Maximum growth rates (μmax) calculated for each derivative strain and parental strain DSM33110. A.
Figure 3:
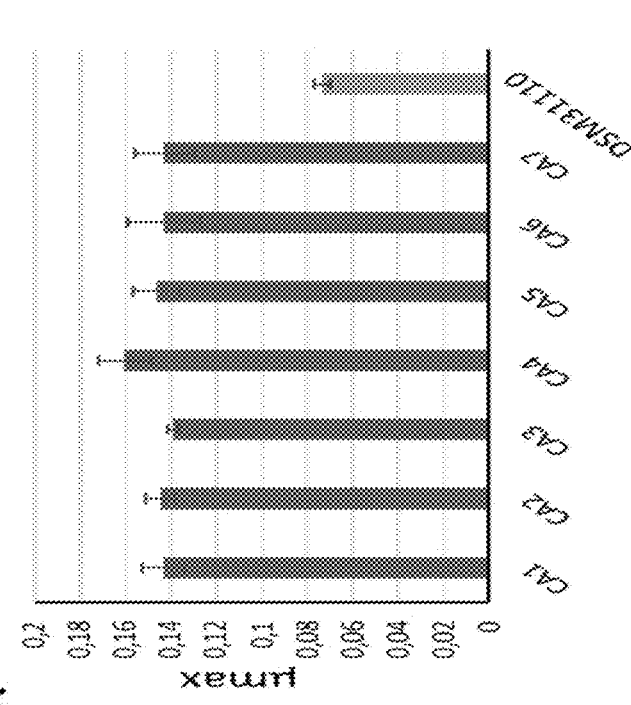

To compare growth profiles and growth rates between adapted derivatives and the parental strain, 2×958 clones (plus parental strain DSM33110) were inoculated into 96-deep-well plates containing either MSgg or MS-Rex medium. Growth experiments were performed in a Growth Profiler at 21° C. Data obtained allowed identification of the faster growing derivatives and selection of best 30 individual clones. Growth curves were then determined in triplicates to ensure reproducibility. Growth rates were calculated applying the slope function to OD600 recorded values in exponential phase. Umax values correspond to change in OD600 unit per hour ($h^{-1}$) FIG. 2 shows average growth data from the seven best derivatives developed from each growth media. FIG. 3 shows calculated maximum growth rates (µmax) for derivatives and mother strain DSM33110.

Example 3—Genome Sequencing and SNP Analysis of Improved Derivatives

Final selected clones (2×7) were deposited in the CHCC collection and genome sequenced. Single nucleotide polymorphism (SNP) analysis was performed by comparing the genome sequences of the selected cold adapted strains to the DSM33110 genome sequence.

| CHCC number | Strain name | SNPs analysis | Frequency |
|---|---|---|---|
| CHCC32528 | CA1 | 8-amino-7-oxononanoate synthase (EC2.3.1.47): p.Pro314Ser (BioF) | 8 out of 14 (57%) |
| | | YbgE homologue-Branched-chain amino acid aminotransferase (EC2.6.1.42): p.Asp3fs | 2 out of 14 (14%) |
| CHCC32529 | CA2 | 8-amino-7-oxononanoate synthase (EC2.3.1.47): p.Ala64Val (BioF) | 8 out of 14 (57%) |
| | | Flagellar biosynthesis protein FliP: p.Lys156Glu | 1 out of 14 |
| | | Smc-superfamily protein: p.Ser163fs | 1 out of 14 |
| CHCC32530 | CA3 | Heat-inducible transcription repressor HrcA: p.Gln6* | 5 out of 14 |
| | | SNP in region upstream of BioWAFDB operon. Maybe affecting the promoter region | 2 out of 14 (10/14) |
| CHCC36494 | CA4 | 8-amino-7-oxononanoate synthase (EC2.3.1.47): p.Arg37Trp (BioF) | 8 out of 14 (57%) |
| | | Flagellar biosynthesis protein FlhA: p.Ala128Val | 3 out of 14 (21%) |
| CHCC36495 | CA5 | SNP in region upstream of BioWAFDB operon. Maybe affecting the promoter region | 2 out of 14 (9/14) |

-continued

| CHCC number | Strain name | SNPs analysis | Frequency |
|---|---|---|---|
| CHCC36496 | CA6 | 8-amino-7-oxononanoate synthase (EC 2.3.1.47): p.Pro314Ser (BioF) | 8 out of 14 (57%) |
| | | YbgE homologue-Branched-chain amino acid aminotransferase (EC 2.6.1.42): p.Phe195fs | 2 out of 14 (14%) |
| | | Flagellar biosynthesis protein FlhB: p.Glu16fs | 1 out of 14 (7/14) |
| CHCC36497 | CA7 | Heat-inducible transcription repressor HrcA: p.Pro314Thr | 5 out of 14 |
| | | ABC transporter permease protein: p.Lys624fs | 1 out of 14 |
| CHCC36751 | CAREX1 | Glycogen synthase, ADP-glucose transglucosylase (EC 2.4.1.21): p.Lys150fs | 1 out of 14 |
| | | Heat-inducible transcription repressor HrcA: p.Gln11* | 5 out of 14 |
| CHCC36752 | CAREX2 | 8-amino-7-oxononanoate synthase (EC 2.3.1.47): p.Ala244Val (BioF) | 8 out of 14 (57%) |
| | | Flagellar biosynthesis protein FlhA: p.Ala128Val | 3 out of 14 (21%) |
| CHCC36753 | CAREX3 | Heat-inducible transcription repressor HrcA: p.Gln11* | 5 out of 14 |
| CHCC36754 | CAREX4 | 8-amino-7-oxononanoate synthase (EC2.3.1.47): p.Pro314Ser (BioF) | 8 out of 14 (57%) |
| | | SNP in promoter region of YpfA homologue, receptor of c-di-GMP: T to C | 2 out of 14 |
| | | Flagellar basal-body rod protein FlgG: p.Gln152* | 2 out of 14 |
| | | Hypothetical protein in operon with YteA, a RsbR paralogue:: p.Phe5fs. | 1 out of 14 |
| CHCC36755 | CAREX5 | 8-amino-7-oxononanoate synthase (EC 2.3.1.47): p.Asp309Gly (BioF) | 8 out of 14 (57%) |
| | | Transcriptional regulator GabR of GABA utilization: p.Arg30Leu | 1 out of 14 |
| | | SNP in promoter region of YpfA homologue, receptor of c-di-GMP: T to C | 2 out of 14 |
| | | Flagellar basal-body rod protein FlgG: p.Gln152* | 2 out of 14 |
| CHCC36756 | CAREX6 | 8-amino-7-oxononanoate synthase (EC 2.3.1.47): p.Arg37Trp | 8 out of 14 (57%) |
| | | Flagellar biosynthesis protein FlhA: p.Ile182fs and several other SNPs | 3 out of 14 (21%) |
| CHCC36757 | CAREX7 | Heat-inducible transcription repressor HrcA: p.Gln11* | 5 out of 14 |

Table 1. SNP analysis and ORF target identification. Table contains information linking cold adapted derivatives ID/name with the corresponding CHCC number. SNPs identity and frequency with which they are found are summarized.

Out of 14 cold adapted DSM33110 derivatives sequenced, 8 showed mutations targeting the bioF orf. bioF encodes an 8-amino-7-oxononanoate synthase (EC2.3.1.47), enzyme in the biotin cofactor biosynthetic pathway. See below for physiological interpretation of the SNPs identified.

Genome sequencing results revealed the presence of several SNPs (found in 5 out of 14 derivatives) within the orf hrcA, encoding the heat-inducible transcriptional repressor HrcA. In most cases the identified mutations correspond to stop codons, and only in one of the mutant strains we identified an amino acid change Pro314 to Thr. Most likely all those mutations render an inactive repressor.

Example 4—Growth Advantage Specificity Analysis

To assess whether the growth improvement phenotype was restricted to a specific growth medium composition or low temperatures, we compare the growth profiles of cold-adapted derivatives with the parental strain DSM33110 in complex media (LB and BHI) at 30° C. temperature.

Higher biomass yields and faster growth rates were observed for the cold adapted derivatives, suggesting that the mutations do not only help the strains to grow at low temperatures. During the adaptive evolution process we have selected for fast growers and derivatives that reach higher yields.

Example 5—Plant Growth Promotion Experiments

Plant growth promotion efficiency was compared between the derivative strains at 22° C. and 15° C. using A. thaliana Col-0 plants, in a gnotobiotic system based on the use of 24-well plates filled with plant growth medium solidified with agar. Based on the results from three independent experiments, both in soil and agar systems, derivative strains CA4, CA6 and CAREX1 were selected (CHCC36494, CHCC36496, and CHCC36751, respectively) as the best cold adapted DSM33110 derivatives. Results shown in FIG. 5.

To further evaluate the plant fitness promotion effect of cold adapted selected derivatives, a series of experiments were setup by the application team. Plant growth promotion efficiency was compared between derivative strains using A. thaliana plants in a soil system. Experiments were performed in plant growth chambers. Two different strain combinations containing cold adapted improved derivatives CA4 and CA6 were compared with the parental strain in their ability to promote A. thaliana plant growth. Strains B. paralicheniformis CHCC36494 (CA4) and CHCC36496 (CA6) were co-inoculated with 2 different Bacillus subtilis strains, as indicated in FIG. 19. A. thaliana seedlings were germinated and pre-grown in potting soil for 7 days prior inoculation. Bacterial cultures were grown over-night the day before inoculation. In the morning of inoculation day, bacterial cultures were diluted and grown to $OD_{600}$ 1 in LB broth. Bacterial cells were then washed and resuspended into 10 mM $MgSO_4$ buffer at $OD_{600}$ 0.01. Plants were inoculated with 1e6 CFUs (8 plant replicates per strain), comparing the results from control non-inoculated plants with the parental strain and cold adapted derivatives. Plants grew in growth chambers for 2 weeks, with 16 h light/8 h dark photoperiod at two different temperatures (22° C. and 15° C.) to evaluate the performance of these strains under lower, suboptimal Ta conditions. Shoot fresh weight quantification was done 2 weeks post-inoculation. Results obtained showed an increase in plant growth for all treatments compared to non-inoculated plants, with a more relevant increase being observed for the two combinations containing the cold adapted improved derivative CA6 (19%-40% and 36%-36% increase, at 22° C. and 15° C. temperature, respectively). Both at 22° C. and 15° C., strain combinations containing derivative CA6 (CHCC36496) returned the best results. Nevertheless, only one strain combination showed statistically significant results at 15° C. compared to non-inoculated plants. Therefore, strain combination CA6 (CHCC36496) plus *B. subtilis* DSM33015 was selected to carry on additional testing in crop plants and field trials.

Example 6—Physiological Interpretation of MoA Associated with Identified SNPs BioF—Biotin (also known as vitamin H) is a covalently bound enzyme cofactor required by all forms of life. In 5 out the 8 mutated sequences, the genotypic change renders a protein with an amino acid change from Pro 314 to Ser. In the other 3 mutated sequences the amino acid changes are different (Ala244 to Val, Asp300 to Gly and Arg37 to Trp). Homology searches, ClustalW alignments, and protein 3D structural modelling of the BioF DSM33110 amino acid sequence suggest that selected SNPs result in amino acid changes that most likely are not part of the catalytic site (1) (FIG. 6). How those SNPs affect the activity of the BioF enzyme and intracellular levels of biotin is currently under investigation.

Biotin is an essential cofactor required for diverse key metabolic enzymes that carry out carboxylation and decarboxylation reactions in fatty acid synthesis, amino acid metabolism and gluconeogenesis (2). In *B. cereus*, limiting amounts of biotin were reported to restrict growth and alter the cell membrane fatty acid composition (3). In *Bacillus* spp., the first intermediate in fatty acid and phospholipid synthesis is malonyl-CoA. Malonyl-CoA is synthesized from acetyl-CoA by the acetyl-CoA carboxylase, encoded on the accBC genes. The accBC operon from *Bacillus* codes for two subunits of acetyl-CoA carboxylase, biotin carboxyl-carrier and biotin carboxylase. In addition, a direct correlation between the levels of transcription of the fatty acid accBC genes and the rate of cellular growth was reported in *B. subtilis* (4)

HrcA—HrcA has previously been described in *B. subtilis* as the transcriptional repressor of the class I heat-shock genes, the HrcA regulon (5). The HrcA regulon consists of just two operons, the heptacistronic dnaK operon and the bicistronic groE (FIG. 7). Both operons encode for molecular chaperons and respond to heat stress. HrcA binds to the inverted repeats located in both operons and known as CIRCE (Controlling inverted repeat of chaperon expression) element. DnaK, DnaJ, GrpE and GroES-GroEL are chaperons over-expressed in response to both cold and high temperature treatments (Schumann, W. 2003). A *B. subtilis* hrcA knockout causes high constitutive expression of both class I heat-shock operons in the absence of heat-shock. In addition, deletion of hrcA in *B. subtilis* helps the strain to resume growth faster after a temperature change (heat or cold shock). Accordingly, HrcA over-expression has the opposite effect and cells are less capable to respond to temperature shifts (6).

Genome analysis of cold adapted derivatives identified mutations affecting the hrcA orf. Those SNPs corresponded in most cases to stop codons, and only in one of the mutant strains we identified an amino acid change Pro314 to Thr. Most likely all those mutations render an inactive repressor, which will consequently allow overexpression of the two operons in the regulon.

CONCLUSION

To summarize, strains developed from *B. paralichenifor-mis* (DSM33110) with increased growth rates and higher biomass yields at different temperatures were developed following an adaptive laboratory evolution campaign. 14 different derivatives were selected, and their genomes sequenced to identify the acquired genotypic changes. Derivative strains were characterized physiologically and tested for performance in plant growth experiments.

Based on our results, specific mechanisms to explain the observed phenotypic differences with the parental strain is presented.

In addition, these evolution experiments have supplied/contributed with new *Bacillus* strains showing improved properties in plant growth promotion.

In a preferred aspect, the term bioF gene as used herein is intended to mean the BioF region 8-amino-7-oxononanoate synthase (EC_2.3.1.47). In yet a preferred aspect, the term hrcA gene as used herein is intended to mean the Heat-inducible transcription repressor HrcA.

DEPOSITS and EXPERT SOLUTION

The applicant requests that a sample of the deposited microorganisms stated below may only be made available to an expert, until the date on which the patent is granted.

The applicant deposited *Bacillus paralicheniformis* parent strain was deposited as DSM33110 on May 8, 2019 at Leibniz Institute DSMZ—German Collection of Microorganisms and Cell Cultures, Inhoffenstr. 7B, D-38124 Braunschweig.

The applicant deposited the strains derived from the parent strain on Aug. 14, 2019 at Leibniz Institute DSMZ—German Collection of Microorganisms and Cell Cultures, Inhoffenstr. 7B, D-38124 Braunschweig as:

*Bacillus paralicheniformis* CHCC32530=DSM 33238
*Bacillus paralicheniformis* CHCC36494=DSM 33239
*Bacillus paralicheniformis* CHCC36496=DSM 33240
*Bacillus paralicheniformis* CHCC36751=DSM 33241
*Bacillus paralicheniformis* CHCC36753=DSM 33242
*Bacillus paralicheniformis* CHCC36754=DSM 33243
*Bacillus paralicheniformis* CHCC36755=DSM 33244
*Bacillus paralicheniformis* CHCC32530 (DSM 33238),
*Bacillus paralicheniformis* CHCC36494 (DSM 33239),
*Bacillus paralicheniformis* CHCC36496 (DSM 33240),
*Bacillus paralicheniformis* CHCC36751 (DSM 33241),
*Bacillus paralicheniformis* CHCC36753 (DSM 33242),
*Bacillus paralicheniformis* CHCC36754 (DSM 33243) and
*Bacillus paralicheniformis* CHCC36755 (DSM 33244) were deposited at Leibniz-Institut DSMZ (Deutsche Sammlung von Mikroorganismen und Zellkulturen GmbH, Inhoffenstrasse 7B, D-38124 Braunschweig, Germany) on Aug. 14, 2019, under the terms of the Budapest Treaty on the International Recognition of the Deposit of Microorganisms for the Purposes of Patent Procedure and in compliance with 37 C.F.R. 1.801-1.809, including 37 C.F.R. 1.808(a)(2). Each deposit represents of substantially pure culture of the deposited strain. The deposits are available as required by foreign patent laws in countries wherein counterparts of the subject application or its progeny are filed. However, it is to be understood that the availability of a deposit does not constitute a license to practice the presently claimed subject matter in derogation of patent rights granted by governmental action.

SEQUENCES

Forming part of present description is the sequence listing attached hereto. As specified therein, the sequences
SEQ ID NO:1 defines the hrcA nucleotide sequence
SEQ ID NO:2 defines the HrcA protein sequence
SEQ ID NO:3 defines the bioF nucleotide sequence
SEQ ID NO:4 defines the BioF protein sequence.

The invention claimed is:

1. A composition comprising *Bacillus paralicheniformis* strain CHCC36494, deposited at Leibniz Institute DSMZ—German Collection of Microorganisms and Cell Cultures, Inhoffenstr. 7B, D-38124 Braunschweig (DSMZ) as accession number DSM 33239 in an agrochemically acceptable carrier.

2. The composition of claim 1, comprising about $1 \times 10^2$ to about $1 \times 10^9$ colony forming units of *Bacillus paralicheniformis* strain CHCC36494 per gram of said composition.

3. The composition of claim 1, comprising at least $1 \times 10^9$ colony forming units of *Bacillus paralicheniformis* strain CHCC36494 per gram of said composition.

4. The composition of claim 1, further comprising one or more additional microorganisms.

5. The composition of claim 1, further comprising one or more additional strains of *Bacillus*.

6. The composition of claim 1, further comprising one or more strains of *Bacillus subtilis*.

7. The composition of claim 1, further comprising one or more chemical insecticides, fungicides, nematicides and/or bactericides.

8. The composition of claim 1, further comprising one or more plant extracts.

9. The composition of claim 1, further comprising one or more plant growth regulators.

10. The composition of claim 1, further comprising one or more fertilizers.

11. A kit comprising the composition of claim 1 and instructions for applying said composition to a plant seed, to a plant growth medium and/or to a plant.

12. A plant seed that is at least partially coated with the composition of claim 1.

13. The plant seed of claim 12, comprising about $1 \times 10^2$ to about $1 \times 10^9$ colony forming units of *Bacillus paralicheniformis* strain CHCC36494.

14. A kit comprising a plurality of plant seeds that are at least partially coated with the composition of claim 1 and instructions for using said plurality of seeds.

15. The kit of claim 14, comprising about $1 \times 10^2$ to about $1 \times 10^9$ colony forming units of *Bacillus paralicheniformis* strain CHCC36494 per seed.

16. A method comprising applying the composition of claim 1 to a plant seed.

17. A method comprising introducing the composition of claim 1 into a plant growth medium.

18. A method comprising applying the composition of claim 1 to a plant.

19. A method comprising treating a plant or plant seed with the composition of claim 1 in an amount effective to enhance growth of said plant or plant seed.

20. A method comprising treating a plant or plant seed with the composition of claim 1 in an amount effective to confer protection to said plant or plant seed against one or more plant pathogens.

21. The method of claim 20, wherein said one or more plant pathogens comprises one or more *Meloidogyne, Pratylenchus, Heterodera, Globodera, Ditylenchus, Tylenchulus, Xiphinema, Radopholus, Rotylenchulus, Helicotylenchus* and/or *Belonolaimus*.

* * * * *

SEQUENCE LISTING

<160> NUMBER OF SEQ ID NOS: 7

<210> SEQ ID NO 1
<211> LENGTH: 1032
<212> TYPE: DNA
<213> ORGANISM: Bacillus paralicheniformis
<220> FEATURE:
<223> OTHER INFORMATION: Heat-inducible transcription repressor HrcA
      nucleotide sequence in B. paralicheniformis CHCC3809

<400> SEQUENCE: 1
atgttaacaa atcgtcagct gttaatcttg caggttatcg tcaacgattt cattcgttca      60
gctcagccgg taggatcaag aacgctttcc aaaaaggaag atatcacatt cagctcagca     120
acgatcagaa acgaaatggc tgacttggaa gagctcggtt ttattgaaaa aacccactca     180
tcttcaggcc ggattccttc tgaaaaaggc tatcgctatt atgtcgatca tctgctttca     240
cccggaaagc tgtcaaaaac ggacttgaac attattcatt cggttttcaa agaaaaaatc     300
tttgaactcg aaaaagcggt gcagaagtcg gctcaagtgc tgtctgatct gacaaattat     360
acatcgattg tcctcggtcc gagactgagc gaaaatcatc tcaaacagat ccagattgtg     420
ccgattcagc ctaagaaggc cgttgccatt ctagtaacga ataccggcca tgtcgagaat     480
aaaacgatca actttccggc ggaggtcaat ctttccgatc tcgaaaagct ggtgaatata     540
ttaaatgaac gccttagagg cgtgccgatc tcagagctga agacaggat tttcaaagag     600 gtcgtcatct tcttaaagtc gcatatccaa aattacgata cgattttaca cgggctcggc     660
gcaacgctgg attcatctgt tcaaaccgac cggctgtttt tcggcggcaa gattaatatg     720
ctgaatcagc ccgaatttca cgatattgac agagtgaaat cgctattgtc gctcattgag     780
aaagaacagg agcttctccg gctctttcag tcgactgagt ccggaattac cattaaaatc     840
ggcaaggaaa acgactatga agaaatggaa aactgcagcc tgattaccgc gacatacacg     900
gtcggttcaa aacagatcgg ctccatcgcg gtcatcgggc cgacgcgcat ggactactcc     960
cgcgtcgtcg gtttgcttca gcacgtatca tctgacttgt caaaagcgtt gacaagtttg    1020
tatgatgggt aa                                                        1032

<210> SEQ ID NO 2
<211> LENGTH: 343
<212> TYPE: PRT
<213> ORGANISM: Bacillus paralicheniformis
<220> FEATURE:
<223> OTHER INFORMATION: Heat-inducible transcription repressor HrcA
      protein sequence in B. paralicheniformis CHCC3809

<400> SEQUENCE: 2

Met Leu Thr Asn Arg Gln Leu Leu Ile Leu Gln Val Ile Val Asn Asp
1               5                   10                  15

Phe Ile Arg Ser Ala Gln Pro Val Gly Ser Arg Thr Leu Ser Lys Lys
            20                  25                  30

Glu Asp Ile Thr Phe Ser Ser Ala Thr Ile Arg Asn Glu Met Ala Asp
        35                  40                  45

Leu Glu Glu Leu Gly Phe Ile Glu Lys Thr His Ser Ser Ser Gly Arg
    50                  55                  60

Ile Pro Ser Glu Lys Gly Tyr Arg Tyr Tyr Val Asp His Leu Leu Ser
65                  70                  75                  80

Pro Gly Lys Leu Ser Lys Thr Asp Leu Asn Ile Ile His Ser Val Phe
                85                  90                  95

Lys Glu Lys Ile Phe Glu Leu Glu Lys Ala Val Gln Lys Ser Ala Gln

-continued

```
                  100                 105                 110
Val Leu Ser Asp Leu Thr Asn Tyr Thr Ser Ile Val Leu Gly Pro Arg
        115                 120                 125

Leu Ser Glu Asn His Leu Lys Gln Ile Gln Ile Val Pro Ile Gln Pro
    130                 135                 140

Lys Lys Ala Val Ala Ile Leu Val Thr Asn Thr Gly His Val Glu Asn
145                 150                 155                 160

Lys Thr Ile Asn Phe Pro Ala Glu Val Asn Leu Ser Asp Leu Glu Lys
                165                 170                 175

Leu Val Asn Ile Leu Asn Glu Arg Leu Arg Gly Val Pro Ile Ser Glu
            180                 185                 190

Leu Lys Asp Arg Ile Phe Lys Glu Val Val Ile Phe Leu Lys Ser His
        195                 200                 205

Ile Gln Asn Tyr Asp Thr Ile Leu His Gly Leu Gly Ala Thr Leu Asp
    210                 215                 220

Ser Ser Val Gln Thr Asp Arg Leu Phe Phe Gly Gly Lys Ile Asn Met
225                 230                 235                 240

Leu Asn Gln Pro Glu Phe His Asp Ile Asp Arg Val Lys Ser Leu Leu
                245                 250                 255

Ser Leu Ile Glu Lys Glu Gln Glu Leu Leu Arg Leu Phe Gln Ser Thr
            260                 265                 270

Glu Ser Gly Ile Thr Ile Lys Ile Gly Lys Glu Asn Asp Tyr Glu Glu
        275                 280                 285

Met Glu Asn Cys Ser Leu Ile Thr Ala Thr Tyr Thr Val Gly Ser Lys
    290                 295                 300

Gln Ile Gly Ser Ile Ala Val Ile Gly Pro Thr Arg Met Asp Tyr Ser
305                 310                 315                 320

Arg Val Val Gly Leu Leu Gln His Val Ser Ser Asp Leu Ser Lys Ala
                325                 330                 335

Leu Thr Ser Leu Tyr Asp Gly
                340
```

```
<210> SEQ ID NO 3
<211> LENGTH: 1152
<212> TYPE: DNA
<213> ORGANISM: Bacillus paralicheniformis
<220> FEATURE:
<223> OTHER INFORMATION: BioF region 8-amino-7-oxononanoate synthase
      (EC_2.3.1.47) nucleotide sequence in B. paralicheniformis CHCC3809

<400> SEQUENCE: 3
gtgcccattg acgaatggct cagcagtcgg ctcgccagga cgaaggcagc cgggctttac        60
cgctcgctta aaccgcctca agctgtcgcg gaagcgaaac gtacgaatcg ggcgtcaaac       120
gattatttga gcctggcgaa cgacaaacgg ctgattcacg ccgcagaaac ggcgcttcgc       180
cgctttggag ccgggagcac agggtcaagg ctgacgtccg gcaataccga atggcatgaa       240
aaacttgagc ggaaaatcgc cggttttaag cagacagaag ccgctctctt gttttcaagc       300
ggatatttgg ccaatatcgg cgtgctttcg tctttgcctg aaaaaggaga cgtcatatta       360
agcgatcaat tgaaccatgc gagcatcatc gacggctgcc gcctttcaaa agctgatacg       420
gttgtttacc gccacacgga tatgaatgat cttgaagaaa aactccgcac cgcacagagc       480
cgtgctcgct gttttattgt gacagacggc gtgttcagca tggacggcac aattgcaccg       540
cttgacgaaa tcatgctcct tgccaagcgg taccgggcct ttgtcatcgt tgatgatgcc       600
cacgcaacag gggttttggg agatgccggc aggggaacgg gcgagtattt cggcgtctcc       660
```

-continued

```
ccagatgttg tgatcggcac gttaagtaaa gctgtaggcg cggaaggcgg cttcgtcgcg      720
ggctctaaag cattgatcga ttttttgctg aatcatgcga gaacgtttat ctttcaaacg      780
gctgtcccgc ccgcaagctg tgcggcggca tgcagagctt tagacatcat taaagacagc      840
cgggataaac gccggctttt gcaatcatcg gtgaccacga tcaaacgggg tctcgaggat      900
atcgggttta cggtcaaggg agaagatacg ccgatcatac ccgttatgat cggagaccct      960
caaaaagccg ttcgatttgc aaacggcctc aaggagaaag ggattgaggc cccggccatc     1020
cgcccgccga ctgttgcgga aggagagagc cgaatcaggc tgaccgtcac cgcagatcgc     1080
aagttaagag atattgaagc tctattagag gggtttaaat tagtgggaag agagttgaac     1140
ttggtgaaat ga                                                        1152
```

<210> SEQ ID NO 4
<211> LENGTH: 383
<212> TYPE: PRT
<213> ORGANISM: Bacillus paralicheniformis
<220> FEATURE:
<223> OTHER INFORMATION: BioF region 8-amino-7-oxononanoate synthase
    (EC_2.3.1.47) protein sequence in B. paralicheniformis CHCC3809

<400> SEQUENCE: 4

```
Met Pro Ile Asp Glu Trp Leu Ser Ser Arg Leu Ala Arg Thr Lys Ala
1               5                   10                  15

Ala Gly Leu Tyr Arg Ser Leu Lys Pro Pro Gln Ala Val Ala Glu Ala
            20                  25                  30

Lys Arg Thr Asn Arg Ala Ser Asn Asp Tyr Leu Ser Leu Ala Asn Asp
        35                  40                  45

Lys Arg Leu Ile His Ala Ala Glu Thr Ala Leu Arg Arg Phe Gly Ala
    50                  55                  60

Gly Ser Thr Gly Ser Arg Leu Thr Ser Gly Asn Thr Glu Trp His Glu
65                  70                  75                  80

Lys Leu Glu Arg Lys Ile Ala Gly Phe Lys Gln Thr Glu Ala Ala Leu
                85                  90                  95

Leu Phe Ser Ser Gly Tyr Leu Ala Asn Ile Gly Val Leu Ser Ser Leu
            100                 105                 110

Pro Glu Lys Gly Asp Val Ile Leu Ser Asp Gln Leu Asn His Ala Ser
        115                 120                 125

Ile Ile Asp Gly Cys Arg Leu Ser Lys Ala Asp Thr Val Val Tyr Arg
    130                 135                 140

His Thr Asp Met Asn Asp Leu Glu Glu Lys Leu Arg Thr Ala Gln Ser
145                 150                 155                 160

Arg Ala Arg Cys Phe Ile Val Thr Asp Gly Val Phe Ser Met Asp Gly
                165                 170                 175

Thr Ile Ala Pro Leu Asp Glu Ile Met Leu Leu Ala Lys Arg Tyr Arg
            180                 185                 190

Ala Phe Val Ile Val Asp Asp Ala His Ala Thr Gly Val Leu Gly Asp
        195                 200                 205

Ala Gly Arg Gly Thr Gly Glu Tyr Phe Gly Val Ser Pro Asp Val Val
    210                 215                 220

Ile Gly Thr Leu Ser Lys Ala Val Gly Ala Glu Gly Gly Phe Val Ala
225                 230                 235                 240

Gly Ser Lys Ala Leu Ile Asp Phe Leu Leu Asn His Ala Arg Thr Phe
                245                 250                 255

Ile Phe Gln Thr Ala Val Pro Pro Ala Ser Cys Ala Ala Ala Cys Arg
```

-continued

```
                 260                 265                 270

Ala Leu Asp Ile Ile Lys Asp Ser Arg Asp Lys Arg Arg Leu Leu Gln
                 275                 280                 285

Ser Ser Val Thr Thr Ile Lys Arg Gly Leu Glu Asp Ile Gly Phe Thr
                 290                 295                 300

Val Lys Gly Glu Asp Thr Pro Ile Ile Pro Val Met Ile Gly Asp Pro
305                 310                 315                 320

Gln Lys Ala Val Arg Phe Ala Asn Gly Leu Lys Glu Lys Gly Ile Glu
                 325                 330                 335

Ala Pro Ala Ile Arg Pro Pro Thr Val Ala Glu Gly Glu Ser Arg Ile
                 340                 345                 350

Arg Leu Thr Val Thr Ala Asp Arg Lys Leu Arg Asp Ile Glu Ala Leu
                 355                 360                 365

Leu Glu Gly Phe Lys Leu Val Gly Arg Glu Leu Asn Leu Val Lys
                 370                 375                 380
```

<210> SEQ ID NO 5
<211> LENGTH: 383
<212> TYPE: PRT
<213> ORGANISM: Escherichia coli K12

<400> SEQUENCE: 5

```
Met Ser Trp Gln Glu Lys Ile Asn Ala Ala Leu Asp Ala Arg Arg Ala
1               5                   10                  15

Ala Asp Ala Leu Arg Arg Arg Tyr Pro Val Ala Gln Gly Ala Gly Arg
                20                  25                  30

Trp Leu Val Ala Asp Asp Arg Gln Tyr Leu Asn Phe Ser Ser Asn Asp
                35                  40                  45

Tyr Leu Gly Leu Ser His His Pro Gln Ile Ile Arg Ala Trp Gln Gln
        50                  55                  60

Gly Ala Glu Gln Phe Gly Ile Gly Ser Gly Gly Ser Gly His Val Ser
65                  70                  75                  80

Gly Tyr Ser Val Val His Gln Ala Leu Glu Glu Glu Leu Ala Glu Trp
                85                  90                  95

Leu Gly Tyr Ser Arg Ala Leu Leu Phe Ile Ser Gly Phe Ala Ala Asn
                100                 105                 110

Gln Ala Trp Ile Ala Ala Met Met Ala Lys Glu Asp Arg Ile Ala Ala
        115                 120                 125

Asp Arg Leu Ser His Ala Ser Leu Leu Glu Ala Ala Ser Leu Ser Pro
        130                 135                 140

Ser Gln Leu Arg Arg Phe Ala His Asn Asp Val Thr His Leu Ala Arg
145                 150                 155                 160

Leu Leu Ala Ser Pro Cys Pro Gly Gln Gln Met Val Val Thr Glu Gly
                165                 170                 175

Val Phe Ser Met Asp Gly Asp Ser Ala Pro Leu Ala Glu Ile Gln Gln
                180                 185                 190

Val Thr Gln Gln His Asn Gly Trp Leu Met Val Asp Asp Ala His Gly
        195                 200                 205

Thr Gly Val Ile Gly Glu Gln Gly Arg Gly Ser Cys Trp Leu Gln Lys
        210                 215                 220

Val Lys Pro Glu Leu Leu Val Val Thr Phe Gly Lys Gly Phe Gly Val
225                 230                 235                 240

Ser Gly Ala Ala Val Leu Cys Ser Ser Thr Val Ala Asp Tyr Leu Leu
                245                 250                 255
```

-continued

Gln Phe Ala Arg His Leu Ile Tyr Ser Thr Met Pro Pro Ala Gln Ala
            260                 265                 270

Gln Ala Leu Arg Ala Ser Leu Ala Val Ile Arg Ser Asp Glu Gly Asp
        275                 280                 285

Ala Arg Arg Glu Lys Leu Ala Ala Leu Ile Thr Arg Phe Arg Ala Gly
        290                 295                 300

Val Gln Asp Leu Pro Phe Thr Leu Ala Asp Ser Cys Ser Ala Ile Gln
305                 310                 315                 320

Pro Leu Ile Val Gly Asp Asn Ser Arg Ala Leu Gln Leu Ala Glu Lys
                325                 330                 335

Leu Arg Gln Gln Gly Cys Trp Val Thr Ala Ile Arg Pro Pro Thr Val
            340                 345                 350

Pro Ala Gly Thr Ala Arg Leu Arg Leu Thr Leu Thr Ala Ala His Glu
            355                 360                 365

Met Gln Asp Ile Asp Arg Leu Leu Glu Val Leu His Gly Asn Gly
        370                 375                 380

<210> SEQ ID NO 6
<211> LENGTH: 388
<212> TYPE: PRT
<213> ORGANISM: Bacillus subtilis

<400> SEQUENCE: 6

Met Lys Ile Asp Ser Trp Leu Asn Glu Arg Leu Asp Arg Met Lys Glu
1               5                   10                  15

Ala Gly Val His Arg Asn Leu Arg Ser Met Asp Gly Ala Pro Val Pro
            20                  25                  30

Glu Arg Asn Ile Asp Gly Glu Asn Gln Thr Val Trp Ser Ser Asn Asn
        35                  40                  45

Tyr Leu Gly Leu Ala Ser Asp Arg Arg Leu Ile Asp Ala Ala Gln Thr
    50                  55                  60

Ala Leu Gln Gln Phe Gly Thr Gly Ser Ser Gly Ser Arg Leu Thr Thr
65                  70                  75                  80

Gly Asn Ser Trp Val His Glu Lys Leu Glu Lys Lys Ile Ala Ser Phe
            85                  90                  95

Lys Leu Thr Glu Ala Ala Leu Leu Phe Ser Ser Gly Tyr Leu Ala Asn
            100                 105                 110

Val Gly Val Leu Ser Ser Leu Pro Glu Lys Glu Asp Val Ile Leu Ser
            115                 120                 125

Asp Gln Leu Asn His Ala Ser Met Ile Asp Gly Cys Arg Leu Ser Lys
        130                 135                 140

Ala Asp Thr Val Val Tyr Arg His Ile Asp Met Asn Asp Leu Glu Asn
145                 150                 155                 160

Lys Leu Asn Glu Thr Gln Arg Tyr Lys Arg Arg Phe Ile Val Thr Asp
            165                 170                 175

Gly Val Phe Ser Met Asp Gly Thr Ile Ala Pro Leu Asp Gln Ile Ile
            180                 185                 190

Ser Leu Ala Lys Arg Tyr His Ala Phe Val Val Val Asp Asp Ala His
        195                 200                 205

Ala Thr Gly Val Leu Gly Asp Ser Gly Gln Gly Thr Ser Glu Tyr Phe
        210                 215                 220

Gly Val Cys Pro Asp Ile Val Ile Gly Thr Leu Ser Lys Ala Val Gly
225                 230                 235                 240

Ala Glu Gly Gly Phe Ala Ala Gly Ser Ala Val Phe Ile Asp Phe Leu
                245                 250                 255

-continued

Leu Asn His Arg Thr Phe Ile Phe Gln Thr Ala Ile Pro Pro Ala Ser
            260                 265                 270

Cys Ala Ala Ala His Glu Ala Phe Asn Ile Ile Glu Ala Ser Arg Glu
            275                 280                 285

Lys Arg Gln Leu Leu Phe Ser Tyr Ile Ser Met Ile Arg Thr Ser Leu
            290                 295                 300

Lys Asn Met Gly Tyr Val Val Lys Gly Asp His Thr Pro Ile Ile Pro
305                 310                 315                 320

Val Val Ile Gly Asp Ala His Lys Thr Val Leu Phe Ala Glu Lys Leu
            325                 330                 335

Gln Gly Lys Gly Ile Tyr Ala Pro Ala Ile Arg Pro Pro Thr Val Ala
            340                 345                 350

Pro Gly Glu Ser Arg Ile Arg Ile Thr Ile Thr Ser Asp His Ser Met
            355                 360                 365

Gly Asp Ile Asp His Leu Leu Gln Thr Phe His Ser Ile Gly Lys Glu
            370                 375                 380

Leu His Ile Ile
385

<210> SEQ ID NO 7
<211> LENGTH: 383
<212> TYPE: PRT
<213> ORGANISM: Bacillus paralicheniformis
<220> FEATURE:
<223> OTHER INFORMATION: DSM31110

<400> SEQUENCE: 7

Met Pro Ile Asp Glu Trp Leu Ser Ser Arg Leu Ala Arg Thr Lys Ala
1               5                   10                  15

Ala Gly Leu Tyr Arg Ser Leu Lys Pro Pro Gln Ala Val Ala Glu Ala
            20                  25                  30

Lys Arg Thr Asn Arg Ala Ser Asn Asp Tyr Leu Ser Leu Ala Asn Asp
            35                  40                  45

Lys Arg Leu Ile His Ala Ala Glu Thr Ala Leu Arg Arg Phe Gly Ala
            50                  55                  60

Gly Ser Thr Gly Ser Arg Leu Thr Ser Gly Asn Thr Glu Trp His Glu
65                  70                  75                  80

Lys Leu Glu Arg Lys Ile Ala Gly Phe Lys Gln Thr Glu Ala Ala Leu
                85                  90                  95

Leu Phe Ser Ser Gly Tyr Leu Ala Asn Ile Gly Val Leu Ser Ser Leu
            100                 105                 110

Pro Glu Lys Gly Asp Val Ile Leu Ser Asp Gln Leu Asn His Ala Ser
            115                 120                 125

Ile Ile Asp Gly Cys Arg Leu Ser Lys Ala Asp Thr Val Val Tyr Arg
            130                 135                 140

His Thr Asp Met Asn Asp Leu Glu Glu Lys Leu Arg Thr Ala Gln Ser
145                 150                 155                 160

Arg Ala Arg Cys Phe Ile Val Thr Asp Gly Val Phe Ser Met Asp Gly
                165                 170                 175

Thr Ile Ala Pro Leu Asp Glu Ile Met Leu Leu Ala Lys Arg Tyr Arg
            180                 185                 190

Ala Phe Val Ile Val Asp Asp Ala His Ala Thr Gly Val Leu Gly Asp
            195                 200                 205

Ala Gly Arg Gly Thr Gly Glu Tyr Phe Gly Val Ser Pro Asp Val Val
            210                 215                 220

-continued

```
Ile Gly Thr Leu Ser Lys Ala Val Gly Ala Glu Gly Gly Phe Val Ala
225             230             235                 240

Gly Ser Lys Ala Leu Ile Asp Phe Leu Leu Asn His Ala Arg Thr Phe
                245             250                 255

Ile Phe Gln Thr Ala Val Pro Pro Ala Ser Cys Ala Ala Ala Cys Arg
            260             265             270

Ala Leu Asp Ile Ile Lys Asp Ser Arg Asp Lys Arg Arg Leu Leu Gln
        275             280             285

Ser Ser Val Thr Thr Ile Lys Arg Gly Leu Glu Asp Ile Gly Phe Thr
    290             295             300

Val Lys Gly Glu Asp Thr Pro Ile Ile Pro Val Met Ile Gly Asp Pro
305             310             315                 320

Gln Lys Ala Val Arg Phe Ala Asn Gly Leu Lys Glu Lys Gly Ile Glu
            325             330             335

Ala Pro Ala Ile Arg Pro Pro Thr Val Ala Glu Gly Glu Ser Arg Ile
            340             345             350

Arg Leu Thr Val Thr Ala Asp Arg Lys Leu Arg Asp Ile Glu Ala Leu
        355             360             365

Leu Glu Gly Phe Lys Leu Val Gly Arg Glu Leu Asn Leu Val Lys
    370             375             380
```